US012478728B2

(12) United States Patent
Zhang et al.

(10) Patent No.: US 12,478,728 B2
(45) Date of Patent: Nov. 25, 2025

(54) PERISTALTIC PUMP WITH CONSTANT BIASING FORCE

(71) Applicant: CareFusion 303, Inc., San Diego, CA (US)

(72) Inventors: Lun Zhang, Brea, CA (US); Frank Cai, Ontario, CA (US); Derek Alan Carroll, Carson, CA (US); Siddarth Shevgoor, Mission Viejo, CA (US)

(73) Assignee: CAREFUSION 303, INC., San Diego, CA (US)

( * ) Notice: Subject to any disclaimer, the term of this patent is extended or adjusted under 35 U.S.C. 154(b) by 801 days.

(21) Appl. No.: 17/586,602

(22) Filed: Jan. 27, 2022

(65) Prior Publication Data

US 2022/0233763 A1 Jul. 28, 2022

Related U.S. Application Data

(60) Provisional application No. 63/142,916, filed on Jan. 28, 2021.

(51) Int. Cl.
*A61M 5/142* (2006.01)
*A61M 5/168* (2006.01)
*F04B 43/12* (2006.01)

(52) U.S. Cl.
CPC ...... *A61M 5/1422* (2013.01); *A61M 5/16881* (2013.01); *F04B 43/12* (2013.01)

(58) Field of Classification Search
CPC ............ A61M 5/1422; A61M 5/16881; A61M 5/142; A61M 5/14224; A61M 5/14228; A61M 5/14216; A61M 2005/14533; F04B 43/12; F04B 7/0057; F04B 43/082; F04B 43/1223
See application file for complete search history.

(56) References Cited

U.S. PATENT DOCUMENTS 3,208,396 A * 9/1965 Pitt .......................... F01B 3/106 91/473
2015/0147189 A1 5/2015 Flachbart et al.
2019/0249657 A1* 8/2019 Kamen ............ A61B 17/00234
2020/0054823 A1* 2/2020 Baier ................ A61M 5/14228

FOREIGN PATENT DOCUMENTS

CN 110107486 A 8/2019
GB 2487040 A 7/2012
WO WO-2015041088 A1 3/2015

OTHER PUBLICATIONS

International Search Report and Written Opinion for Application No. PCT/US2022/013919, dated Mar. 14, 2022, 14 pages.

* cited by examiner

*Primary Examiner* — Dung T Ulsh
(74) *Attorney, Agent, or Firm* — MASCHOFF BRENNAN

(57) ABSTRACT

Peristaltic pumps are described herein. In certain embodiments, a peristaltic pump includes a plunger, a first biasing member, and a second biasing member. The plunger is movable to selectively engage a pumping volume of a tubing segment to expand the pumping volume to draw fluid flow into the pumping volume and to contract the pumping volume to conduct fluid flow from the pumping volume. The first biasing member is configured to urge the plunger toward the tubing segment to maintain contact with the tubing segment during the expansion of the pumping volume. The second biasing member is configured to urge the plunger toward the tubing segment to contract the pumping volume.

11 Claims, 19 Drawing Sheets

PERISTALTIC PUMP WITH CONSTANT BIASING FORCE

REFERENCE TO RELATED APPLICATIONS

This application claims priority to U.S. Provisional Patent Application 63/142,916, filed Jan. 28, 2021, the entire disclosure of which is incorporated herein by this reference.

FIELD OF THE INVENTION

The present disclosure generally relates to pumps, and, in particular, to peristaltic pumps.

BACKGROUND

Patients in hospitals often receive medications and medical fluids (e.g., a saline solution or a liquid medication) via infusion using an intravenous ("IV") pump. In some applications, an IV pump uses peristaltic manipulation of a segment of tubing of an IV set to create the flow of medical fluid to the patient.

SUMMARY

The disclosed subject matter relates to peristaltic pumps. In certain embodiments, a peristaltic pump includes a plunger movable to selectively engage a pumping volume of a tubing segment to expand the pumping volume to draw fluid flow into the pumping volume and to contract the pumping volume to conduct fluid flow from the pumping volume; a first biasing member configured to urge the plunger toward the tubing segment to maintain contact with the tubing segment during the expansion of the pumping volume; and a second biasing member configured to urge the plunger toward the tubing segment to contract the pumping volume.

In certain embodiments, a peristaltic pump includes a plunger movable to selectively engage a pumping volume of a tubing segment; a camshaft comprising a plunger cam lobe, wherein the plunger cam lobe is configured to move the plunger between an expansion position to draw fluid flow into the pumping volume and a contraction position to conduct fluid flow from the pumping volume; and a first biasing member configured to urge the plunger toward the tubing segment to maintain contact with the tubing segment during the expansion of the pumping volume.

In certain embodiments, a method is disclosed and comprises expanding a peristaltic pumping volume of a tubing segment; and urging a plunger toward the tubing segment to maintain contact with the tubing segment during the expansion of the pumping volume with a first force.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to administration of medical fluid by utilizing the disclosed peristaltic pumps, it is to be understood that this description is only an example of usage and does not limit the scope of the claims. Various aspects of the disclosed peristaltic pumps may be used in any application where it is desirable to administer the flow of fluid.

Figure 1:
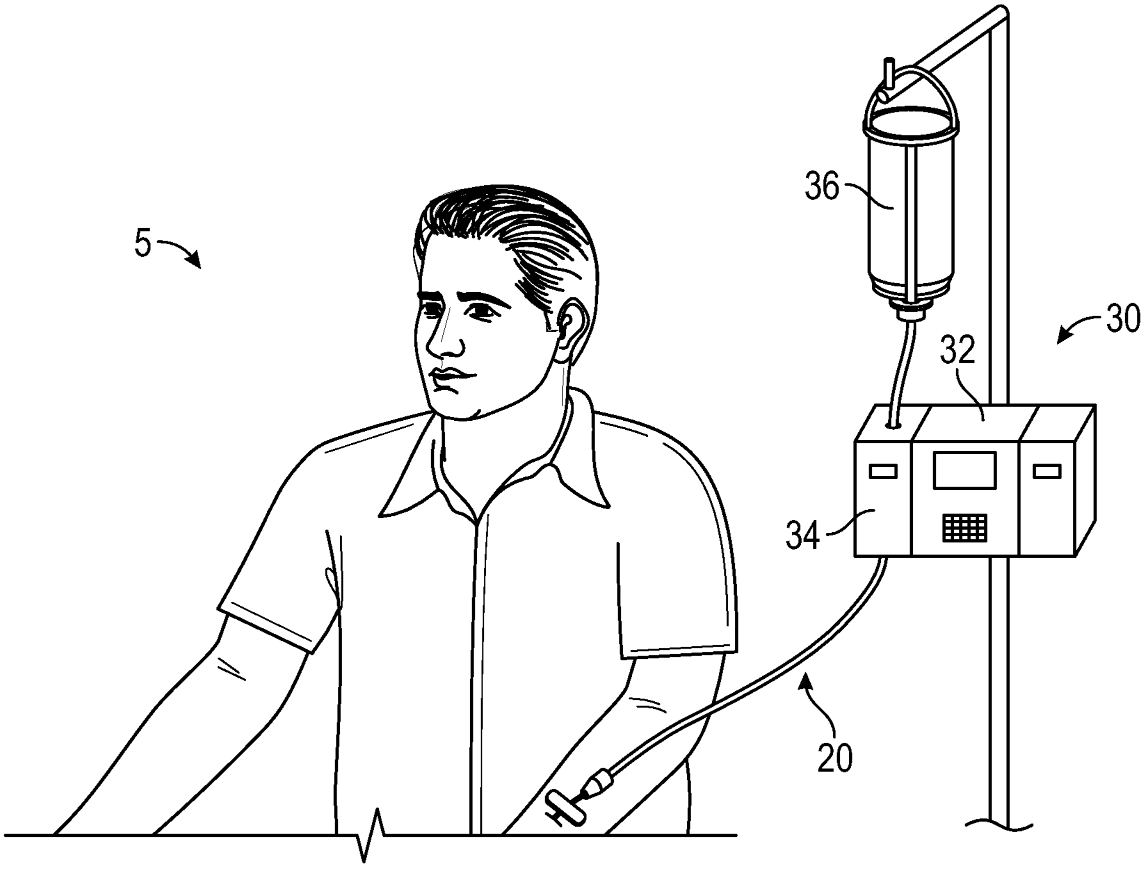
FIG. 1 depicts a patient receiving an infusion of a medical fluid using an IV pump.

FIG. 1 depicts a patient 5 receiving an infusion of a medical fluid using an IV pump 30. In the depicted example, the IV pump 30 is delivering a medical fluid from a fluid container 36 to the patient 5. A fluid container 36 is hung at or above the patient's head and connected via an IV set 20 to the IV pump module 34 and then to the patient 5. In some embodiments, the IV pump 30 includes a control unit 32 and a pumping module 34.

The pumping module 34 can include a peristaltic pump to administer the medical fluid from the fluid container 36 to the patient 5.

During operation of the peristaltic pump, it may be desirable to monitor the volume pumped by the peristaltic pump. In some applications, the peristaltic pump can include a measurement phase between a refill phase and a delivery phase.

The disclosed peristaltic pump can incorporate various measurement mechanisms to allow for monitoring the volume pumped by the peristaltic pump. The disclosed peristaltic pump can include feeler mechanisms, biasing members with various levels of force, and/or split plungers. By utilizing the measurement mechanisms disclosed herein, the peristaltic pump can allow for monitoring without a dedicated measurement phase and/or without generating high internal pressures.

The disclosed peristaltic pump overcomes several challenges discovered with respect to certain measurement approaches utilized with peristaltic pumps. One challenge with certain measurement approaches is that during a dedicated measurement phase, a plunger may apply a large force to a fluid volume confined between an upper valve and a lower valve to measure the fluid volume, pressurizing the fluid volume. Accordingly, the upper valve and the lower valve may apply a large force to the tubing that contains the pressurized fluid volume during measurement, which may damage or cause wear to the tubing. Another challenge with certain measurement approaches is that flow may be discontinued during a dedicated measurement phase, promoting out-gassing of dissolved gases in an infusate. Because damage or wear to the tubing can result in tubing material particulate to dislodge from the tubing and enter a patient's bloodstream and out-gassing of dissolved gases can cause embolisms in a patient, it is advantageous to provide measurement mechanisms that allow for measurement of a fluid volume without a dedicated measurement phase and/or without generating high internal pressures. The disclosed peristaltic pumps provide for measurement of a fluid volume without a dedicated measurement phase and/or without generating high internal pressures during a measurement phase.

Examples of peristaltic pumps that allow for measurement of a fluid volume without a dedicated measurement phase and/or without generating high internal pressures are now described.

Figure 2A:
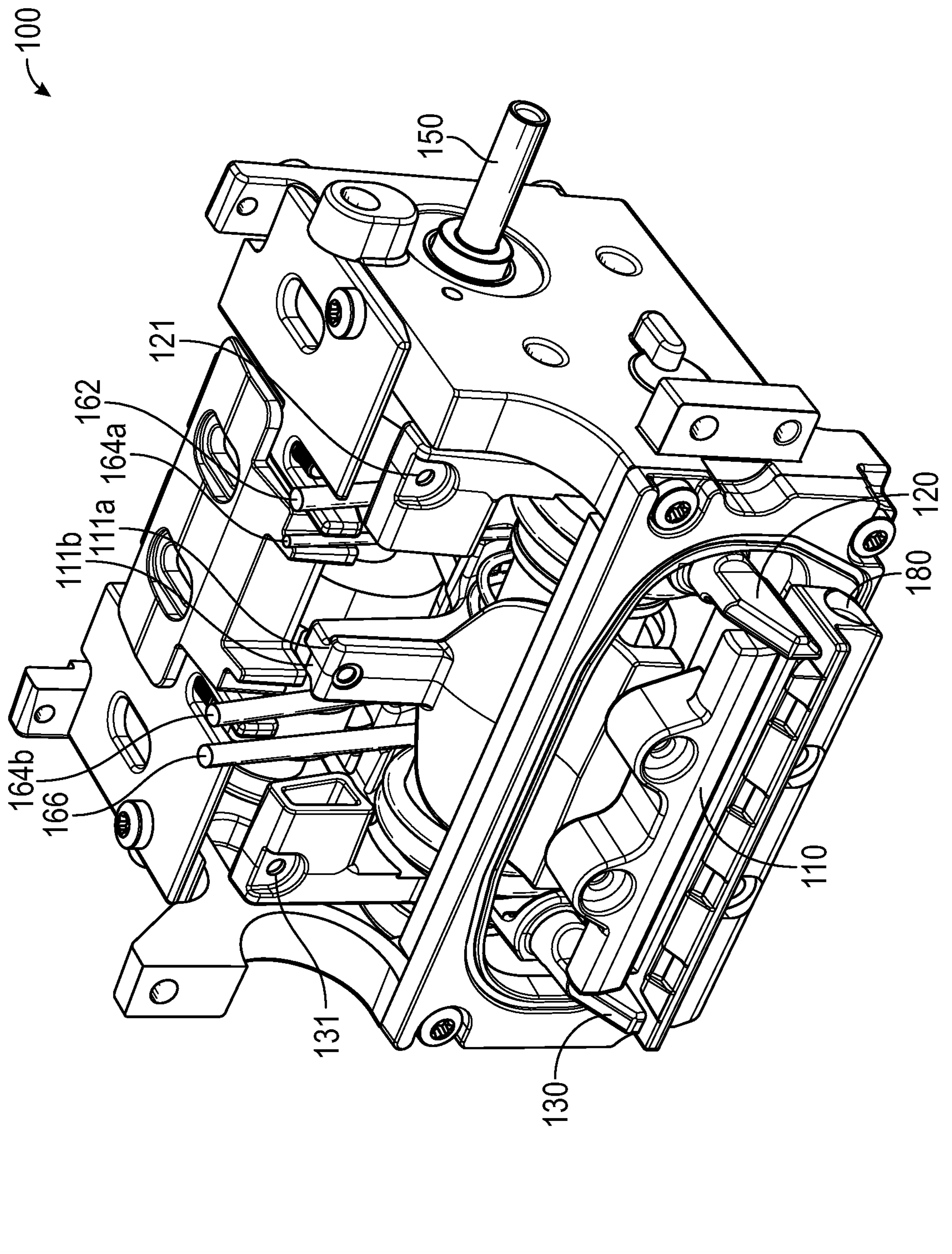
FIG. 2A is a perspective view of a peristaltic pump, in accordance with various aspects of the present disclosure.
Figure 2B:
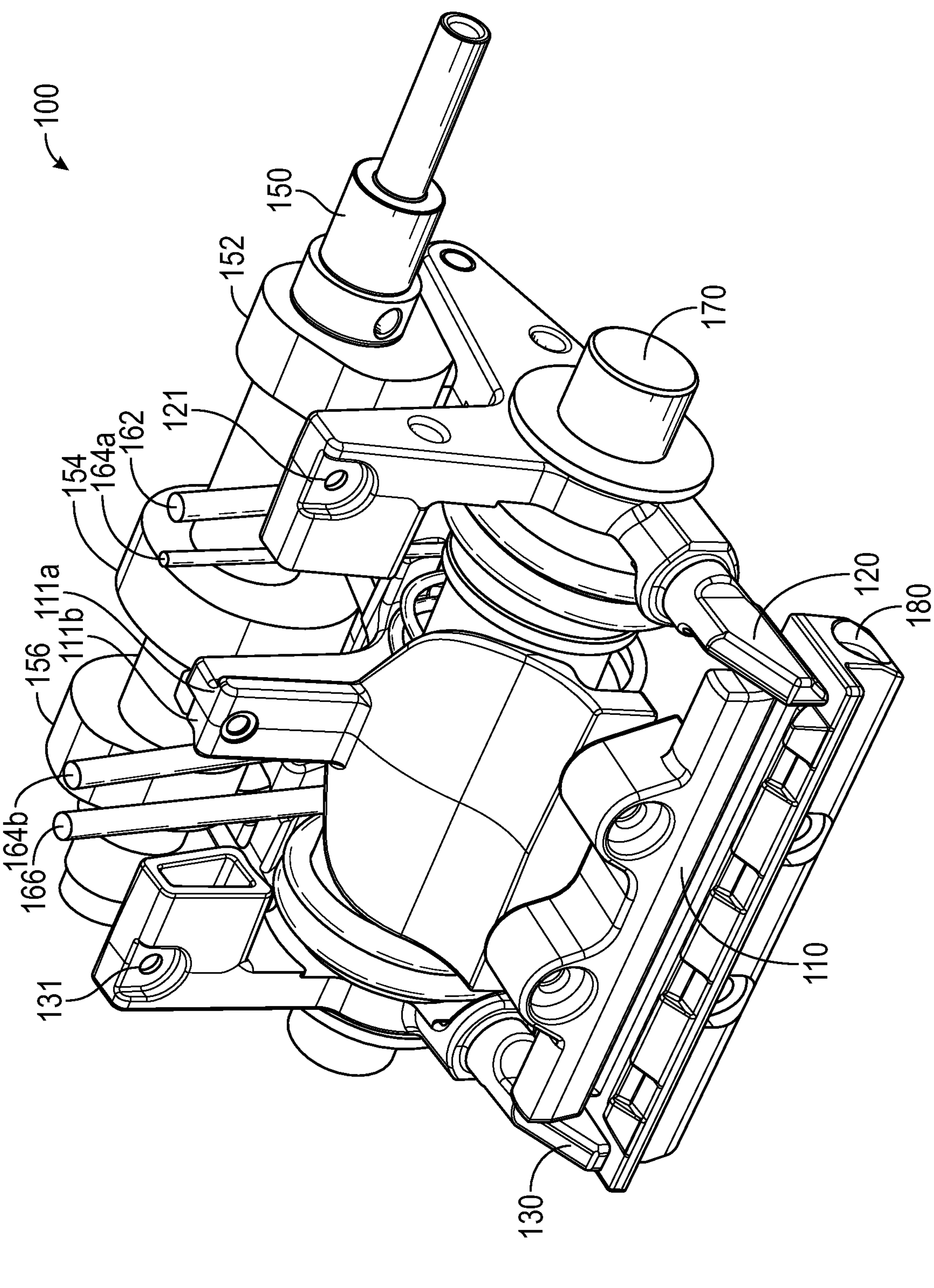
FIG. 2B is a simplified view of the peristaltic pump of FIG. 2A.

FIG. 2A is a perspective view of a peristaltic pump 100, in accordance with various aspects of the present disclosure. FIG. 2B is a simplified view of the peristaltic pump 100 of FIG. 2A. In the depicted example, the peristaltic pump 100 can peristaltically manipulate tubing to create the flow of medical fluid to the patient. In some embodiments, an upstream portion of the tubing is in fluid communication with a source of medical fluid, such as an IV bag or other medical fluid container, and the downstream portion of the tubing is in fluid communication with IV tubing to the patient. In some embodiments, the peristaltic pump 100 repeatedly cycles between a filling phase and a delivery phase to administer fluid to the patient. As described herein, the peristaltic pump 100 allows for volume measurements without requiring a dedicated measurement phase.

In the depicted example, the peristaltic pump 100 includes a plunger 110, an upstream occluder or valve 120, and a downstream occluder or valve 130, each configured to contact and manipulate the tubing to deliver fluid from a fluid source to the patient. In some embodiments, the plunger 110, the upstream valve 120, and the downstream valve 130 can move in coordinated, sequential steps to pump fluid through the tubing. The tubing can be formed from a mechanically resilient material. The tubing can be supported by a backer 180 as the plunger 110, the upstream valve 120, and/or the downstream valve 130 contact and manipulate the tubing.

As described herein, the plunger 110, the upstream valve 120, and/or the downstream valve 130 can be moved by one or more actuators. The movement of actuators that control the plunger 110, the upstream valve 120, and/or the downstream valve 130 can be coordinated, or otherwise sequenced. In the depicted example, the movement of the plunger 110, the upstream valve 120, and/or the downstream valve 130 is cyclical.

Figure 3:
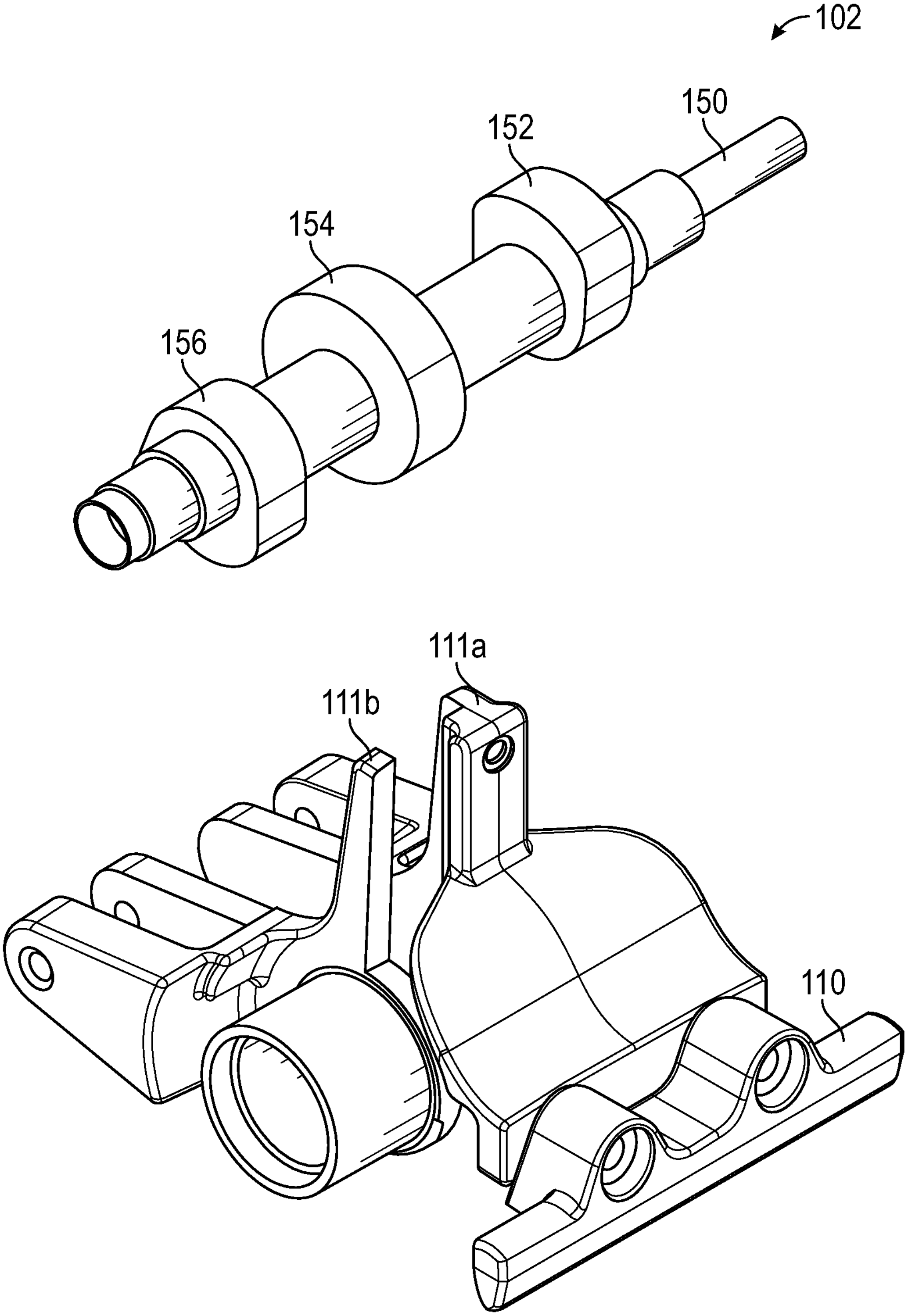
FIG. 3 is an exploded view of components of the peristaltic pump of FIG. 2A.

FIG. 3 is an exploded view of components of the peristaltic pump 100 of FIG. 2A. With reference to FIGS. 2A-3, the peristaltic pump 100 can include a camshaft 150 to actuate the plunger 110, the upstream valve 120, and/or the downstream valve 130. In the depicted example, the camshaft 150 includes one or more cam lobes, such as a plunger cam lobe 154, an upstream valve cam lobe 152, and/or a downstream valve cam lobe 156.

As described herein, the geometry of the respective cam lobes can be shaped or modified to allow for a desired actuation or movement of the plunger 110, the upstream valve 120, and/or the downstream valve 130. For example, portions of a cam lobe with a larger radius can allow for the plunger 110, the upstream valve 120, and/or the downstream valve 130 to open or lift further from the tubing and/or backer 180 while portions of a cam lobe with a smaller radius can allow the plunger 110, the upstream valve 120, and/or the downstream valve 130 to close or otherwise be urged toward the tubing and/or backing.

In some embodiments, the cam lobes of the camshaft 150 actuate one or more rockers to control the plunger 110, the upstream valve 120, and/or the downstream valve 130. As can be appreciated, the geometry of the rockers described herein can be configured to provide a desired actuation ratio between the movement of the plunger 110, the upstream valve 120, and/or the downstream valve 130 and the geometry of the plunger cam lobe 154, upstream valve cam lobe 152, and/or the downstream valve cam lobe 156, respectively. As described herein, certain rockers, such as the second plunger valve rocker 111*b* may move independently or may otherwise not be directly actuated by the camshaft 150. The first plunger valve rocker 111*a*, the second plunger valve rocker 111*b*, the upstream valve rocker 121, and/or the downstream valve rocker 131 can each rotate or pivot about a pivot shaft 170.

In the depicted example, biasing members, such as springs can urge the plunger 110, the upstream valve 120, and/or the downstream valve 130 toward the tubing and/or the backer 180. In some embodiments, biasing members can act upon the rockers to urge the plunger 110, the upstream valve 120, and/or the downstream valve 130 toward the tubing and/or the backer 180. During operation, actuation of the plunger 110, the upstream valve 120, and/or the downstream valve 130 by the camshaft can overcome the biasing force applied by the biasing members to lift or otherwise actuate the plunger 110, the upstream valve 120, and/or the downstream valve 130.

Further, the arrangement or phasing of the cam lobes about the camshaft 150 can be modified to provide a desired sequence of actuation or movement of the plunger 110, the upstream valve 120, and/or the downstream valve 130 as the camshaft 150 is rotated. For example, the plunger cam lobe 154, the upstream valve cam lobe 152, and/or the downstream valve cam lobe 156 can each have a cam profile and/or a relative arrangement that eliminates or otherwise does not include a dedicated measurement phase where the plunger 110 is actuated against a pumping volume of the tubing closed by the upstream valve 120 and the downstream valve 130.

In the depicted example, the peristaltic pump 100 includes a split rocker arrangement with a first plunger valve rocker 111*a* directly coupled to the plunger 110 and a second plunger valve rocker 111*b* configured to act upon the first plunger valve rocker 111*a*. In some embodiments, the first plunger valve rocker 111*a* is spaced apart, decoupled, not aligned, or otherwise not directly actuated by the plunger cam lobe 154. As can be appreciated, the first plunger valve rocker 111*a* and therefore the plunger 110 may be independently moved or actuated separate from the actuation of the plunger cam lobe 154.

In the depicted example, a first plunger biasing member 164*a* can act upon the first plunger valve rocker 111*a* to urge the plunger 110 toward the tubing and/or the backer 180. As can be appreciated, the biasing force applied by the first plunger biasing member 164*a* to the first plunger valve rocker 111*a* and the plunger 110 can be a constant or chronic force that is independent of the rotation of the camshaft 150. During operation, the arrangement of the first plunger valve rocker 111*a* and the first plunger biasing member 164*a* can allow the plunger 110 to maintain contact with the tubing. As can be appreciated, the force applied by the first plunger biasing member 164*a* can be sufficient for the plunger 110 to maintain contact with the tubing without damaging the tubing.

In the depicted example, the position of the plunger 110 can be used to determine the volume of fluid administered by the peristaltic pump 100. During operation, the height of the plunger 110 can be used to determine the height of the pumping volume within the tubing, which can be used to determine the volume of fluid administered by the peristaltic pump 100. Advantageously, the arrangement of the first plunger biasing member 164*a* and the first plunger valve rocker 111*a* allows for the plunger 110 to permit volume measurements without exerting excess force or requiring a dedicated measurement phase.

In the depicted example, the second plunger valve rocker 111*b* is aligned, positioned, or otherwise configured to be actuated by the plunger cam lobe 154. During operation, a portion of the second plunger valve rocker 111*b* can engage or slide along the cam profile of the plunger cam lobe 154 to translate the geometry of the cam profile into movement of the second plunger valve rocker 111*b*. In some embodiments, during certain movements (e.g., during a delivery phase of operation) the second plunger valve rocker 111*b* can engage with the first plunger valve rocker 111*a* to move the plunger 110 relative to the tubing in response to actuation from the plunger cam lobe 154.

In the depicted example, a second plunger biasing member 164*b* can act upon the second plunger valve rocker 111*b* to urge the second plunger valve rocker 111*b* toward the first plunger valve rocker 111*a*. During certain portions of operation (e.g., the delivery phase of operation) the second plunger biasing member 164*b* can force the second plunger valve rocker 111*b* to engage with the first plunger valve rocker 111*a* and urge the plunger 110 toward the tubing and/or the backer 180. As can be appreciated, actuation of the second plunger valve rocker 111*b* by the rotation of the plunger cam lobe 154 can overcome the biasing force to disengage the second plunger valve rocker 111*b* from the first plunger valve rocker 111*a*. Accordingly, the biasing force applied by the second plunger biasing member 164*b* to the first plunger valve rocker 111*a* and/or the plunger 110 can vary in response to the actuation of the second plunger valve rocker 111*b* by the rotation of the plunger cam lobe 154. During operation, the arrangement of the second plunger valve rocker 111*b* and the second plunger biasing member 164*b* relative to the first plunger valve rocker 111*a* and the first plunger biasing member 164*a* allows the peristaltic pump 100 to apply additional force to the plunger during certain portions of operation (e.g., the delivery phase) while allowing the first plunger biasing member 164*a* to maintain a chronic biasing force against the tubing. In some embodiments, the force applied by the second plunger biasing member 164*b* is higher than the biasing force applied by the first plunger biasing member 164*a*. Optionally, the force applied by the second plunger biasing member 164*b* is sufficient to allow fluid delivery. In some embodiments, the first plunger biasing member 164*a* and the second plunger biasing member 164*b* cooperatively provide sufficient force to allow for fluid delivery.

In some embodiments, an upstream valve rocker 121 is coupled to the upstream valve 120 and can move the upstream valve 120 in response to actuation from the upstream valve cam lobe 152. During operation, a portion of the upstream valve rocker 121 can engage or slide along the cam profile of the upstream valve cam lobe 152 to translate the geometry of the cam profile into movement of the upstream valve 120 relative to the tubing.

As illustrated, an upstream valve biasing member 162 can act upon the upstream valve rocker 121 to urge the upstream valve 120 toward the tubing and/or the backer 180. As can be appreciated, actuation of the upstream valve rocker 121 by the rotation of the upstream valve cam lobe 152 can overcome the biasing force to lift or otherwise actuate the upstream valve 120.

Similarly, a downstream valve rocker 131 is coupled to the downstream valve 130 and can move the downstream valve 130 in response to actuation from the downstream valve cam lobe 156. During operation, a portion of the downstream valve rocker 131 can engage or slide along the cam profile of the downstream valve cam lobe 156 to translate the geometry of the cam profile into movement of the downstream valve 130 relative to the tubing.

Similarly, a downstream valve biasing member 166 can act upon the downstream valve rocker 131 to urge the downstream valve 130 toward the tubing and/or the backer 180. As can be appreciated, actuation of the downstream valve rocker 131 by the rotation of the downstream valve cam lobe 156 can overcome the biasing force to lift or otherwise actuate the downstream valve 130.

Figure 4A:
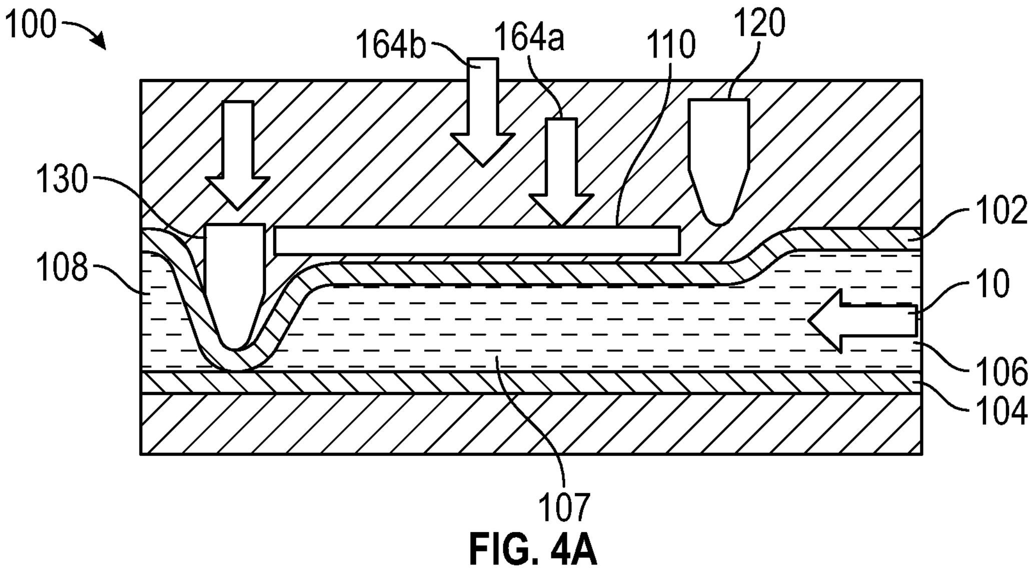
FIG. 4A is an illustration of the peristaltic pump of FIG. 2A in a filling phase, in accordance with various aspects of the present disclosure.

FIG. 4A is an illustration of the peristaltic pump 100 of FIG. 2A in a filling phase, in accordance with various aspects of the present disclosure. During operation, the tubing 102 draws in medical fluid 10 during the filling phase. As illustrated, the plunger 110 is withdrawn or retracted from a compressed portion of the tubing 102, allowing the tubing walls 104 to resiliently expand the pumping volume 107 to an original or expanded state.

In the depicted example, the expansion of the pumping volume 107 draws in fluid into the pumping volume 107. The mechanical resilience of the tubing 102 allows the tubing walls 104 to expand from a compressed state to an expanded state, expanding the pumping volume 107. The rate at which the pumping volume 107 rebounds from a compressed state to an expanded state can determine the amount of fluid that can be drawn into the pumping volume 107 in a given period of time.

As illustrated, during the expansion of the pumping volume 107, the downstream portion 108 of the tubing 102 is blocked, pinched, or otherwise occluded by the downstream valve 130 to prevent or restrict backflow or contamination of fluid into the pumping volume 107.

In the depicted example, the downstream valve 130 is actuated, moved downward, or otherwise engaged to compress the tubing walls 104 of the tubing 102 at the downstream portion 108 to occlude flow through the downstream portion 108 of the tubing 102. The downstream valve 130 can include a beveled engagement portion to contact the tubing 102. When engaged, the downstream valve 130 can prevent or restrict flow or fluid communication from the downstream portion 108 into the pumping volume 107.

During the expansion of the pumping volume 107, medical fluid 10 is drawn into pumping volume 107 from the upstream portion 106 of the tubing 102. As illustrated, during the expansion of the pumping volume 107, the upstream portion 106 of the tubing 102 is unobstructed by the upstream valve 120, permitting medical fluid 10 into the pumping volume 107. During operation, the upstream valve 120 is withdrawn or retracted from a compressed portion of the tubing 102, allowing the tubing walls 104 to resiliently expand the upstream portion 106 to an original or expanded state.

In the depicted example, the expansion of the upstream portion 106 permits the flow of medical fluid 10 into the pumping volume 107. The mechanical resilience of the tubing 102 allows the tubing walls 104 to expand from a compressed state to an expanded state, expanding the cross-sectional profile or flow area of the upstream portion 106. The amount of medical fluid 10 drawn into the pumping volume 107 during the filling phase can be determined by the timing and sequence of the plunger 110, the upstream valve 120, a viscosity of the medical fluid 10, and the mechanical properties of the tubing 102.

Advantageously, and as described herein, the first plunger biasing member 164*a* can maintain a constant or chronic force to allow the plunger 110 to maintain contact with the tubing 102 during the filling phase to permit measurement of the pumping volume. In the depicted example, the force applied by the first plunger biasing member 164*a* can be sufficient to maintain contact with the tubing 102 while allowing for the pumping volume 107 to be filled.

Figure 4B:
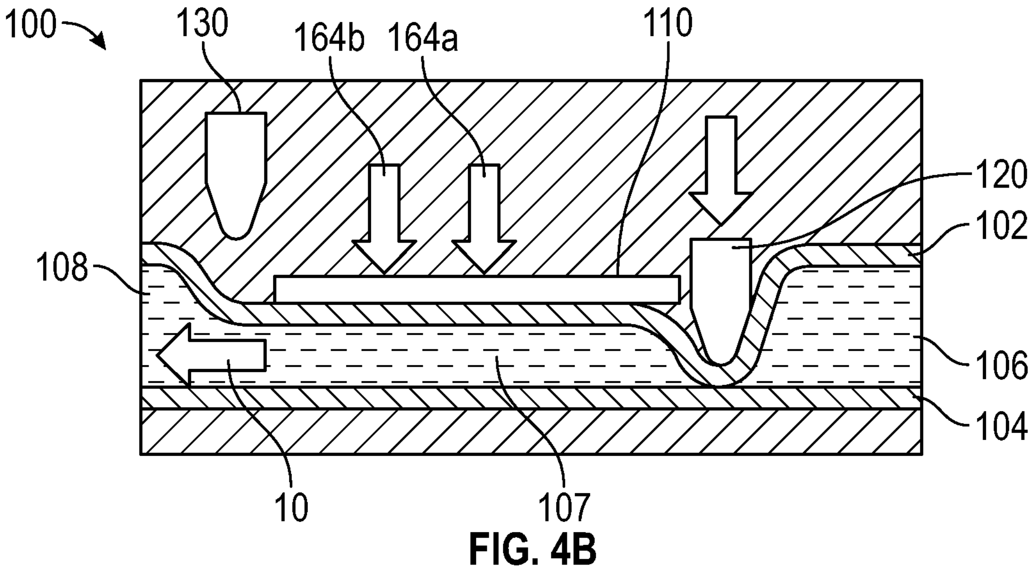
FIG. 4B is an illustration of the peristaltic pump of FIG. 2A in a delivery phase, in accordance with various aspects of the present disclosure.
Figure 4C:
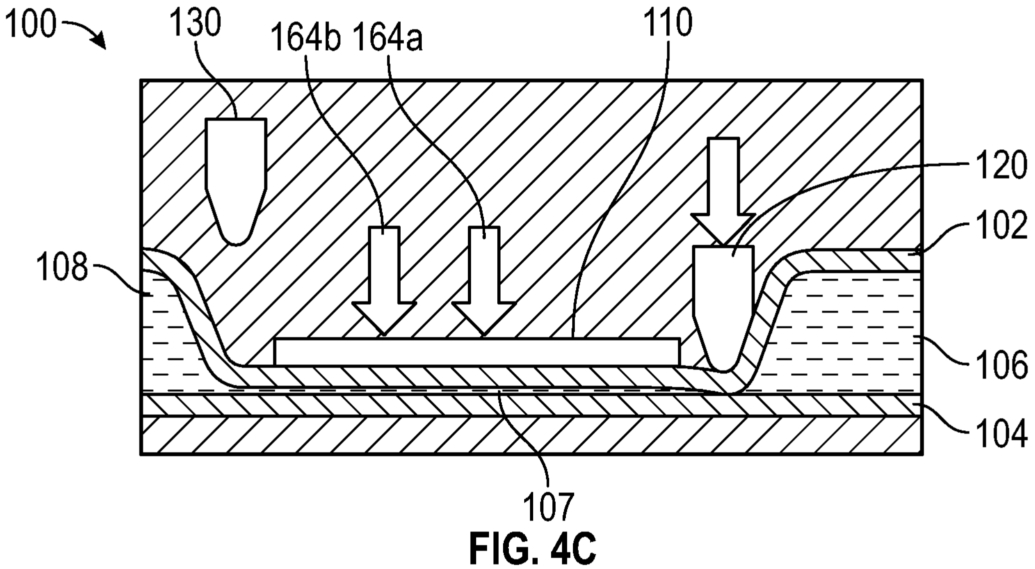
FIG. 4C is an illustration of the peristaltic pump of FIG. 2A in a delivered position, in accordance with various aspects of the present disclosure.

FIG. 4B is an illustration of the peristaltic pump 100 of FIG. 2A in a delivery phase, in accordance with various aspects of the present disclosure. FIG. 4C is an illustration of the peristaltic pump 100 of FIG. 2A in a delivered position, in accordance with various aspects of the present disclosure. With reference to FIGS. 4B and 4C, the peristaltic pump 100 delivers medical fluid through a downstream portion 108 to a downstream location, such as a patient. As illustrated, the plunger 110 is actuated, moved downward, or otherwise engaged to compress the tubing walls 104 of the tubing 102 to compress the pumping volume 107 to a compressed or reduced state.

During operation, the compression of the pumping volume 107 expels or otherwise administers fluid from the pumping volume 107 to a downstream location. The rate of administration of the medical fluid can be controlled by the force and velocity of the plunger 110.

As described herein, the first plunger biasing member 164*a* and the second plunger biasing member 164*b* cooperatively force the plunger 110 to compress the pumping volume 107 to a compressed or reduced state. In some embodiments, the second plunger biasing member 164*b* can force the plunger 110 to compress the pumping volume 107 to a compressed or reduced state without the cooperation of the first plunger biasing member 164*a*.

During administration, the upstream portion 106 of the tubing 102 is blocked, pinched, or otherwise occluded by the upstream valve 120 to prevent or restrict inadvertent fluid flow into the pumping volume 107 and to prevent or restrict backflow of fluid into the medical container from the pumping volume 107.

In the depicted example, the upstream valve 120 is actuated, moved downward, or otherwise engaged to compress the tubing walls 104 of the tubing 102 at the upstream portion 106 to occlude flow through the upstream portion 106 of the tubing 102. The upstream valve 120 can include a beveled engagement portion to contact the tubing 102. When engaged, the upstream valve 120 can prevent or restrict flow or fluid communication between the upstream portion 106 and the pumping volume 107.

During the compression of the pumping volume 107, medical fluid is forced from the pumping volume 107 to a downstream location through the downstream portion 108 of the tubing 102. As illustrated, during the compression of the pumping volume 107, the downstream portion 108 of the tubing 102 is unobstructed by the downstream valve 130, permitting medical fluid 10 to flow out of the tubing 102. During operation, the downstream valve 130 is withdrawn or retracted from a compressed portion of the tubing 102, allowing the tubing walls 104 to resiliently expand the downstream portion 108 to an original or expanded state.

In the depicted example, the expansion of the downstream portion 108 permits the flow of medical fluid 10 out of the pumping volume 107. The mechanical resilience of the tubing 102 allows the tubing walls 104 to expand from a compressed state to an expanded state, expanding the cross-sectional profile or flow area of the downstream portion 108. The rate at which the downstream portion 108 rebounds from a compressed state to an expanded state can limit the size of the flow area or opening out of the pumping volume 107. Therefore, the rate at which the downstream portion 108 rebounds from a compressed state to an expanded state can limit or restrict the amount of fluid that can flow out of the pumping volume 107 in a given period of time.

The amount of medical fluid 10 administered from the pumping volume 107 during the delivery phase can be determined by the timing and sequence of the plunger 110, the downstream valve 130 and the mechanical properties of the tubing 102.

Figure 5A:
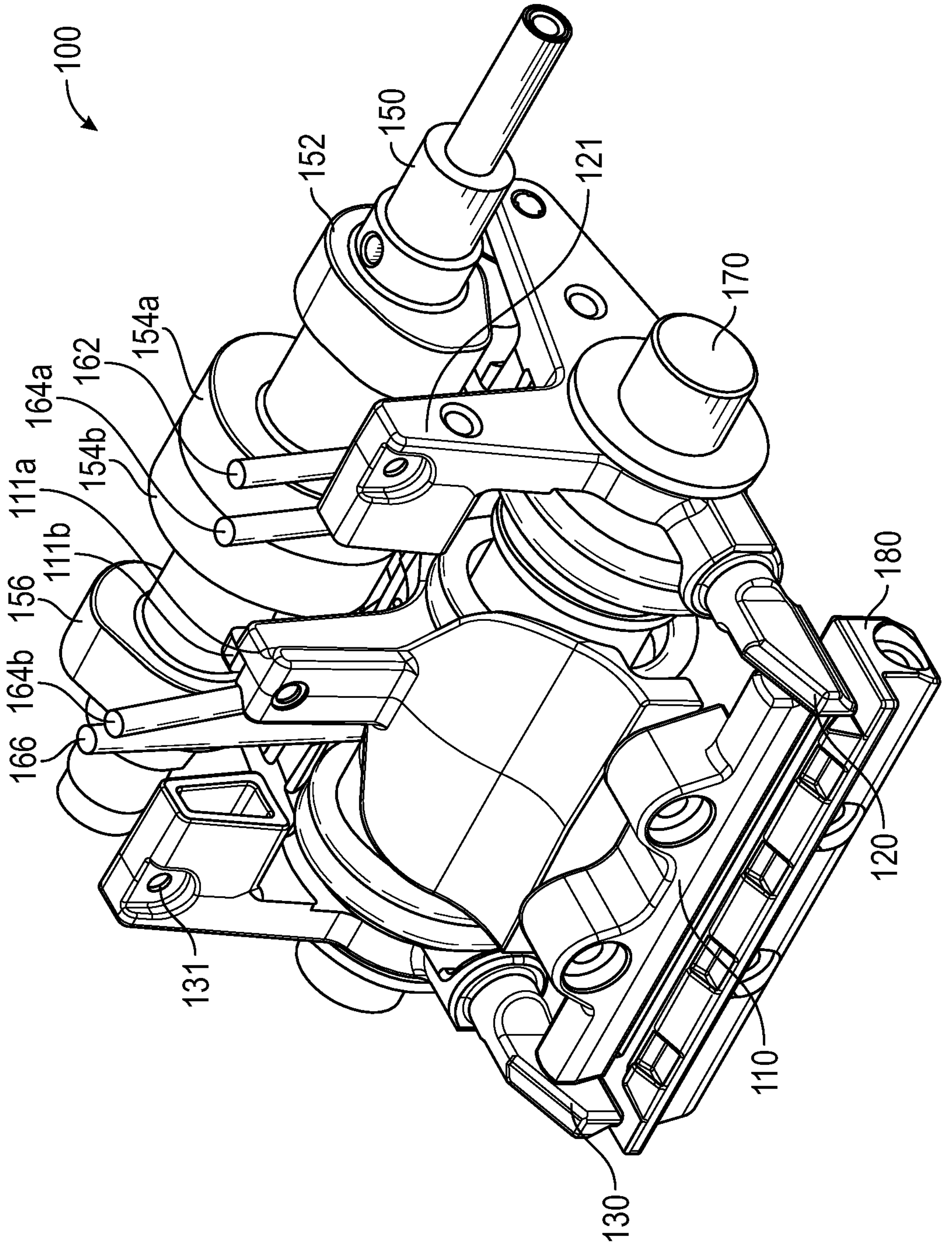
FIG. 5A is a simplified perspective view of a peristaltic pump, in accordance with various aspects of the present disclosure.
Figure 5B:
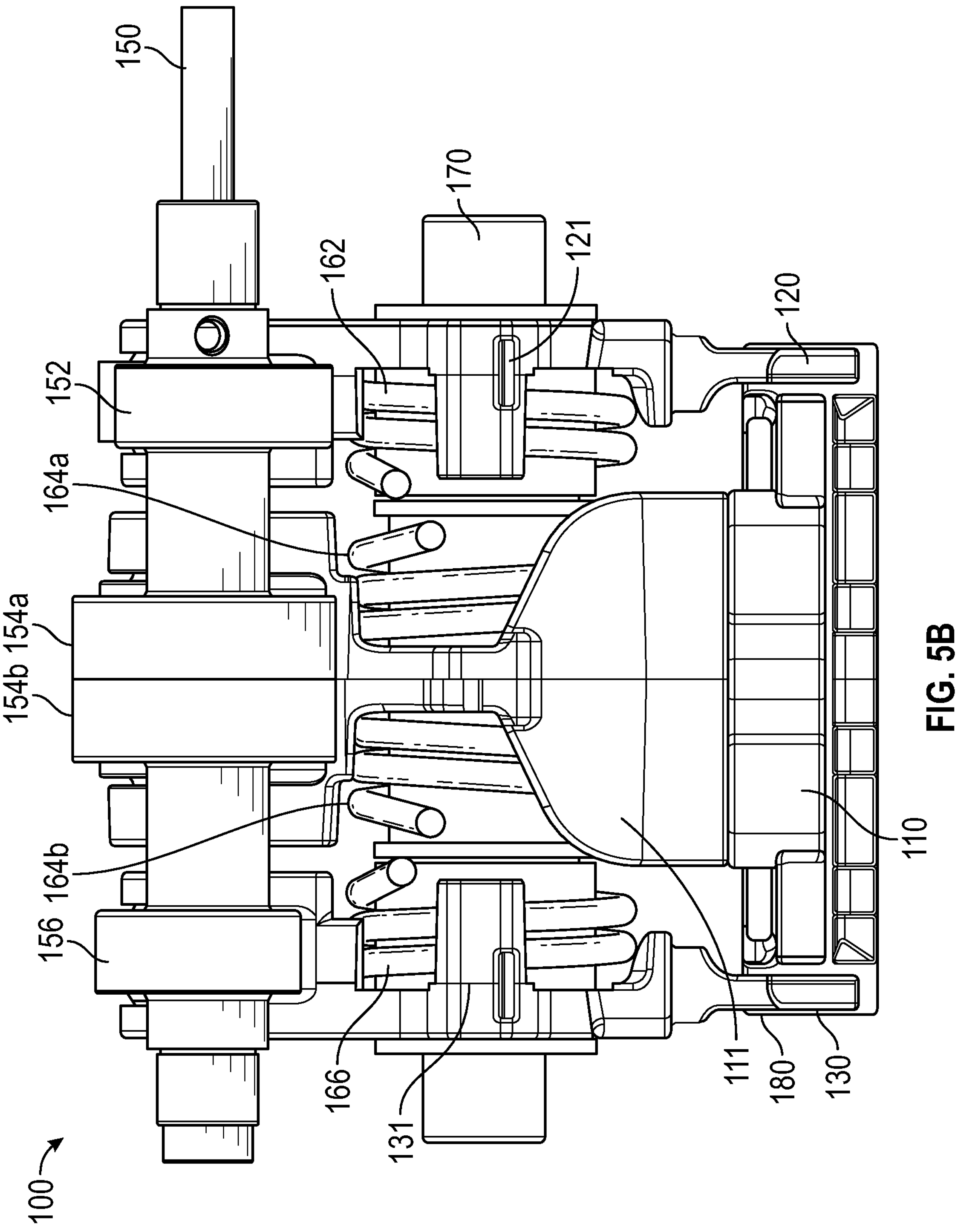
FIG. 5B is a top view of the peristaltic pump of FIG. 5A.
Figure 5C:
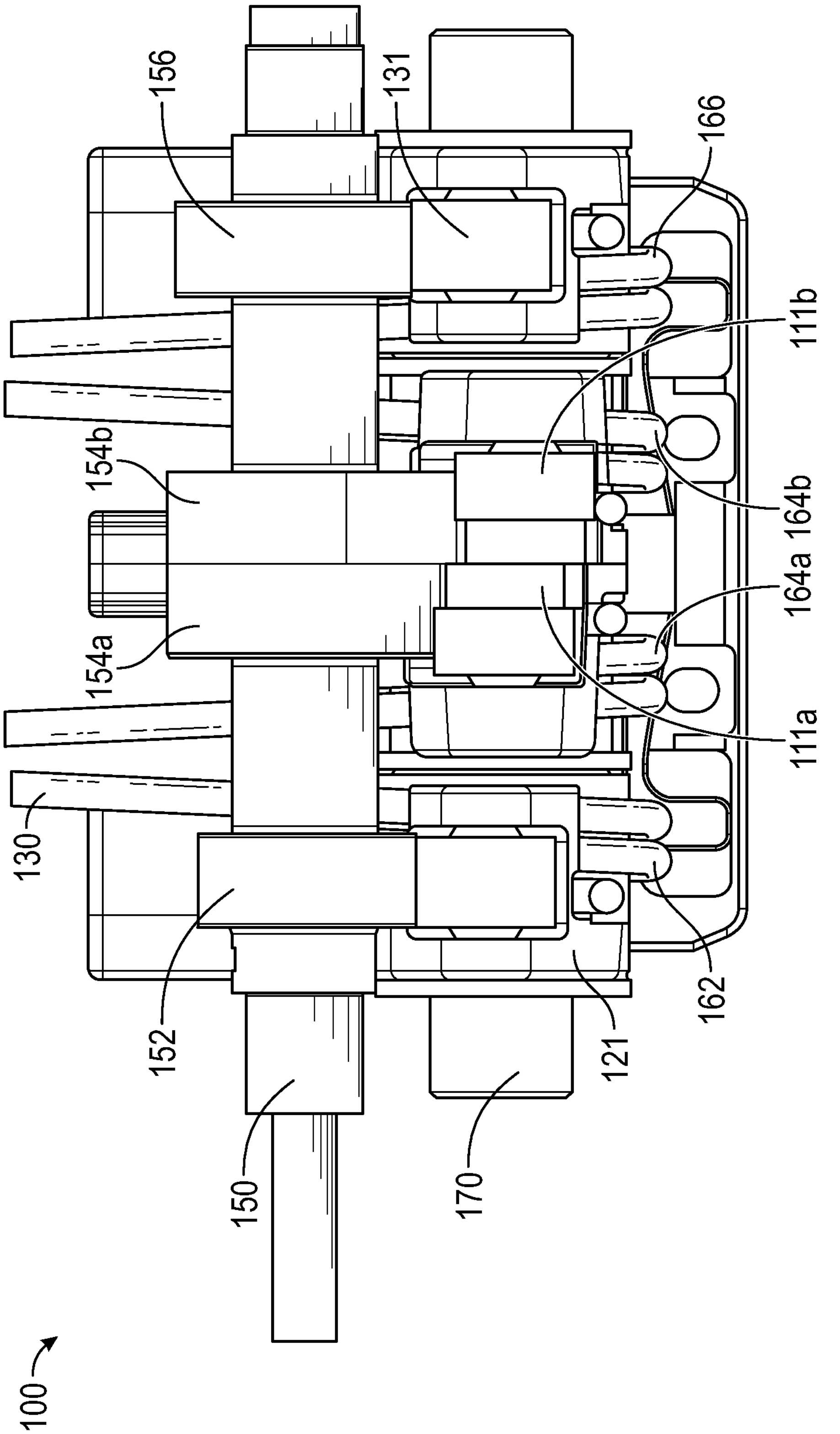
FIG. 5C is a back view of the peristaltic pump of FIG. 5A.
Figure 6:
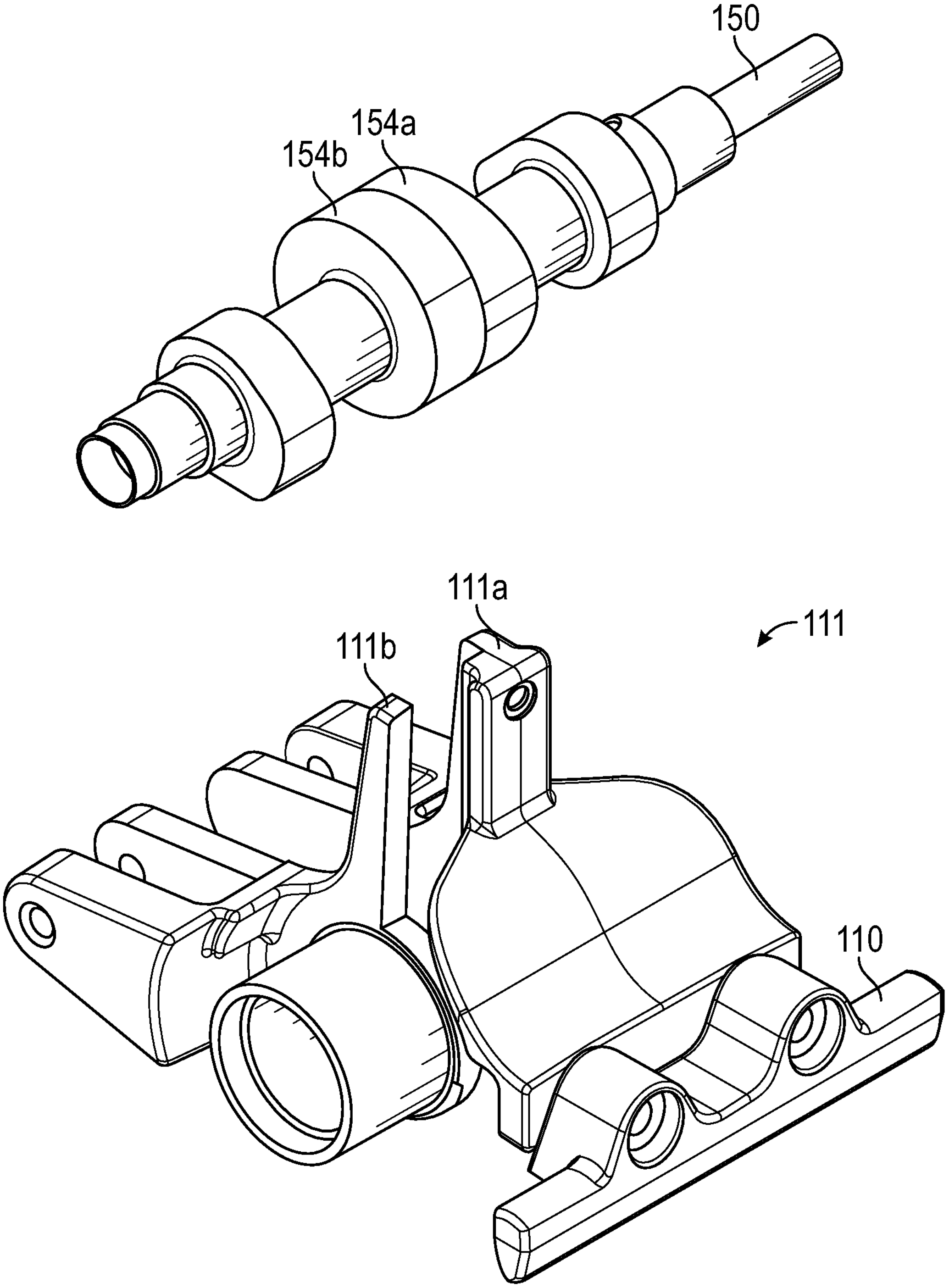
FIG. 6 is an exploded view of components of the peristaltic pump of FIG. 5A.

FIG. 5A is a perspective view of a peristaltic pump 100, in accordance with various aspects of the present disclosure. FIG. 5B is a simplified view of the peristaltic pump 100 of FIG. 5A. FIG. 5C is a back view of the peristaltic pump 100 of FIG. 5A. FIG. 6 is an exploded view of components of the peristaltic pump 100 of FIG. 5A. With reference to FIGS. 5A-6, the peristaltic pump 100 can independently control the operation of the first plunger valve rocker 111*a* and the second plunger valve rocker 111*b* to control the spring or biasing force applied to the plunger 110. Advantageously, the peristaltic pump 100 can be configured to permit volume measurements without exerting excess force during a measurement phase.

As previously described, the peristaltic pump 100 can include a camshaft 150 to actuate the plunger 110, the upstream valve 120, and/or the downstream valve 130. In the depicted example, the camshaft 150 includes one or more cam lobes, such as a first plunger cam lobe 154*a*, a second plunger cam lobe 154*b*, an upstream valve cam lobe 152, and/or a downstream valve cam lobe 156.

In the depicted example, the peristaltic pump 100 includes a split rocker arrangement with a first plunger valve rocker 111*a* directly coupled to the plunger 110 and a second plunger valve rocker 111*b* configured to act upon the first plunger valve rocker 111*a*. In the depicted example, the first plunger valve rocker 111*a* is aligned, positioned, or otherwise configured to be actuated by the first plunger cam lobe 154*a*. During operation, a portion of the first plunger valve rocker 111*a* can engage or slide along the cam profile of the first plunger cam lobe 154*a* to translate the geometry of the cam profile into movement of the first plunger valve rocker 111*a* and the plunger 110. As can be appreciated, the first plunger valve rocker 111*a* and therefore the plunger 110 may be independently moved or actuated separate from the actuation of the second plunger valve rocker 111*b* during certain portions of operation (e.g., a measurement phase).

In the depicted example, a first plunger biasing member 164*a* can act upon the first plunger valve rocker 111*a* to urge the plunger 110 toward the tubing and/or the backer 180. As can be appreciated, actuation of the first plunger valve rocker 111*a* by the rotation of the first plunger cam lobe 154*a* can overcome the biasing force to lift or otherwise actuate the plunger 110 independent of the second plunger valve rocker 111*b*. Therefore, the force applied to the plunger 110 can vary in response to the actuation of the first plunger valve rocker 111*a* by the rotation of the first plunger cam lobe 154*a*.

During operation, the arrangement of the first plunger valve rocker 111*a*, the first plunger cam lobe 154*a*, and the first plunger biasing member 164*a* can allow the plunger 110 to contact the tubing during a measurement phase without administering the fluid within the pumping volume or damaging the tubing.

In the depicted example, the second plunger valve rocker 111*b* is aligned, positioned, or otherwise configured to be actuated by the second plunger cam lobe 154*b*. During operation, a portion of the second plunger valve rocker 111*b* can engage or slide along the cam profile of the second plunger cam lobe 154*b* to translate the geometry of the cam profile into movement of the second plunger valve rocker 111*b*. In some embodiments, during certain movements (e.g., during a delivery phase of operation) the second plunger valve rocker 111*b* can engage with the first plunger valve rocker 111*a* to move the plunger 110 relative to the tubing in response to actuation from the second plunger cam lobe 154*b*.

In the depicted example, a second plunger biasing member 164*b* can act upon the second plunger valve rocker 111*b* to urge the second plunger valve rocker 111*b* toward the first plunger valve rocker 111*a*. During certain portions of operation (e.g., the delivery phase of operation) the second plunger biasing member 164*b* can force the second plunger valve rocker 111*b* to engage with the first plunger valve rocker 111*a* and urge the plunger 110 toward the tubing and/or the backer 180. As can be appreciated, actuation of the second plunger valve rocker 111*b* by the rotation of the second plunger cam lobe 154*b* can overcome the biasing force to disengage the second plunger valve rocker 111*b* from the first plunger valve rocker 111*a*. Accordingly, the biasing force applied by the second plunger biasing member 164*b* to the first plunger valve rocker 111*a* and/or the plunger 110 can vary in response to the actuation of the second plunger valve rocker 111*b* by the rotation of the second plunger cam lobe 154*b*. During operation, the arrangement of the second plunger valve rocker 111*b* and the second plunger biasing member 164*b* relative to the first plunger valve rocker 111*a* and the first plunger biasing member 164*a* allows the peristaltic pump 100 to apply additional force to the plunger during certain portions of operation (e.g., the delivery phase) while allowing the a reduced force during other portions of operation (e.g., the measurement phase). In some embodiments, the force applied by the second plunger biasing member 164*b* is higher than the biasing force applied by the first plunger biasing member 164*a*. Optionally, the force applied by the second plunger biasing member 164*b* is sufficient to allow fluid delivery. In some embodiments, the first plunger biasing member 164*a* and the second plunger biasing member 164*b* cooperatively provide sufficient force to allow for fluid delivery.

Further, the arrangement or phasing of the first plunger cam lobe 154*a* and the second plunger cam lobe 154*b* about the camshaft 150 can be modified to provide a desired sequence of actuation or movement of the first plunger valve rocker 111*a* and the second plunger valve rocker 111*b* as the camshaft 150 is rotated. For example, the cam lobes can each have a cam profile and/or a relative arrangement that includes a measurement phase that applies the plunger to the tubing with a reduced spring force.

Figure 7A:
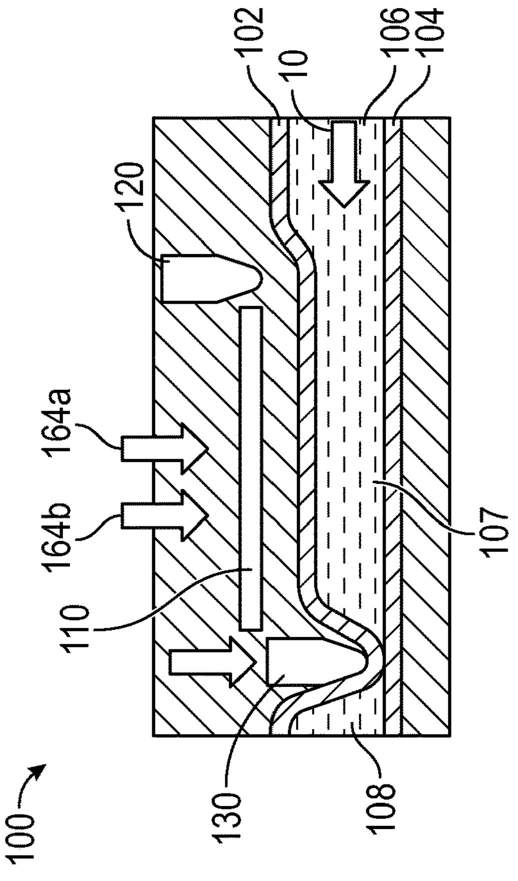
FIG. 7A is an illustration of the peristaltic pump of FIG. 5A in a filling phase, in accordance with various aspects of the present disclosure.

FIG. 7A is an illustration of the peristaltic pump 100 of FIG. 5A in a filling phase, in accordance with various aspects of the present disclosure. During operation, the tubing 102 draws in medical fluid 10 during the filling phase. As illustrated, the plunger 110 is withdrawn or retracted from a compressed portion of the tubing 102, allowing the tubing walls 104 to resiliently expand the pumping volume 107 to an original or expanded state.

In the depicted example, the expansion of the pumping volume 107 draws in fluid into the pumping volume 107. As illustrated, during the expansion of the pumping volume 107, the downstream portion 108 of the tubing 102 is blocked, pinched, or otherwise occluded by the downstream valve 130 to prevent or restrict backflow or contamination of fluid into the pumping volume 107.

During the expansion of the pumping volume 107, medical fluid 10 is drawn into pumping volume 107 from the upstream portion 106 of the tubing 102. As illustrated, during the expansion of the pumping volume 107, the upstream portion 106 of the tubing 102 is unobstructed by the upstream valve 120, permitting medical fluid 10 into the pumping volume 107. During operation, the upstream valve 120 is withdrawn or retracted from a compressed portion of the tubing 102, allowing the tubing walls 104 to resiliently expand the upstream portion 106 to an original or expanded state.

In the depicted example, the expansion of the upstream portion 106 permits the flow of medical fluid 10 into the pumping volume 107. Advantageously, and as described herein, the arrangement of the first plunger cam lobe 154*a* and the second plunger cam lobe 154*b* can prevent the first plunger biasing member 164*a* and the second plunger biasing member from applying force to the plunger 110 and/or the tubing 102 during the filling phase.

Figure 7B:
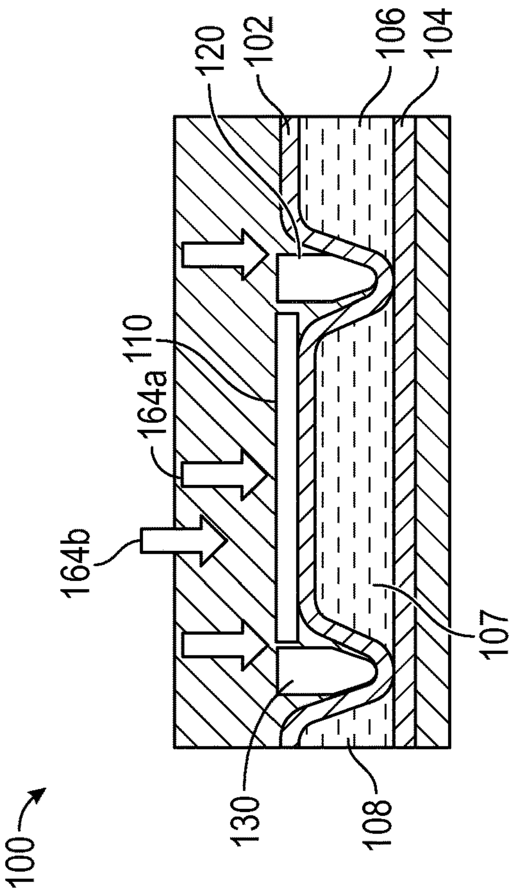
FIG. 7B is an illustration of the peristaltic pump of FIG. 5A in an initial position, in accordance with various aspects of the present disclosure.

FIG. 7B is an illustration of the peristaltic pump 100 of FIG. 5A in an initial or measurement position, in accordance with various aspects of the present disclosure. After filling, the volume of medical fluid within the pumping volume 107 can be measured. As illustrated, the plunger 110 is used to measure the height of the pumping volume 107 and/or the tubing 102 to determine the volume of medical fluid within the pumping volume 107.

During the measurement phase, the downstream portion 108 of the tubing 102 remains blocked, pinched, or otherwise occluded by the downstream valve 130 to prevent or restrict backflow or contamination of fluid into the pumping volume 107. Further, the upstream portion 106 of the tubing 102 is blocked, pinched, or otherwise occluded by the upstream valve 120 to prevent or restrict inadvertent fluid flow into the pumping volume 107 and to prevent or restrict backflow of fluid into the medical container from the pumping volume 107.

Further, during measurement, the first plunger biasing member 164*a* applies a force to the plunger 110 to allow the plunger 110 to contact the tubing 102 to determine the height of the tubing 102 and/or the pumping volume 107. In the depicted example, the force applied by the first plunger biasing member 164*a* can be sufficient to maintain contact with the tubing 102 without creating excess pressure within the pumping volume.

Figure 7C:
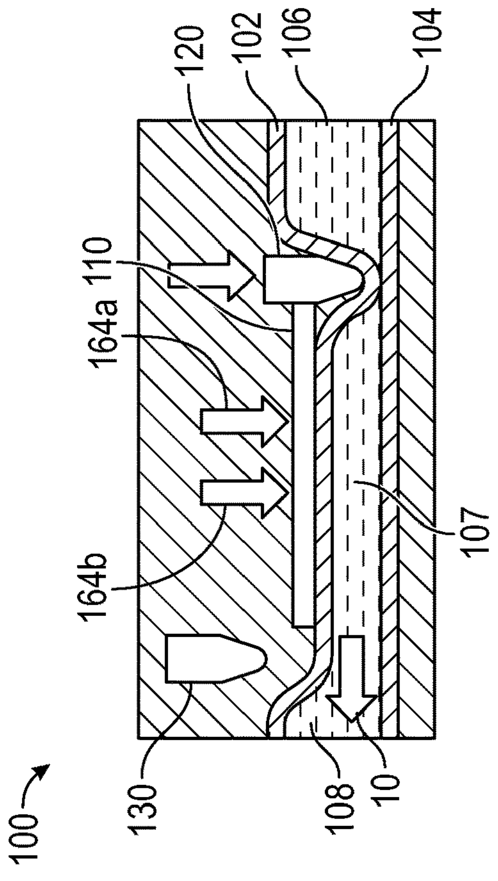
FIG. 7C is an illustration of the peristaltic pump of FIG. 5A in a delivery phase, in accordance with various aspects of the present disclosure.
Figure 7D:
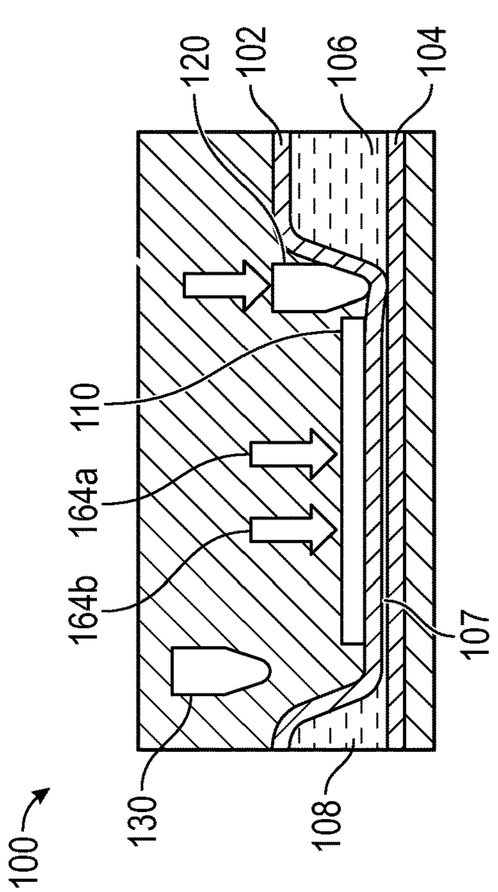
FIG. 7D is an illustration of the peristaltic pump of FIG. 5A in a delivered position, in accordance with various aspects of the present disclosure.

FIG. 7C is an illustration of the peristaltic pump 100 of FIG. 5A in a delivery phase, in accordance with various aspects of the present disclosure. FIG. 7D is an illustration of the peristaltic pump 100 of FIG. 5A in a delivered position, in accordance with various aspects of the present disclosure. With reference to FIGS. 7C and 7D, the peristaltic pump 100 delivers medical fluid through a downstream portion 108 to a downstream location, such as a patient. As illustrated, the plunger 110 is actuated, moved downward, or otherwise engaged to compress the tubing walls 104 of the tubing 102 to compress the pumping volume 107 to a compressed or reduced state.

During operation, the compression of the pumping volume 107 expels or otherwise administers fluid from the pumping volume 107 to a downstream location. The rate of administration of the medical fluid can be controlled by the force and velocity of the plunger 110.

As described herein, the first plunger biasing member 164*a* and the second plunger biasing member 164*b* cooperatively force the plunger 110 to compress the pumping volume 107 to a compressed or reduced state. In some embodiments, the second plunger biasing member 164*b* can force the plunger 110 to compress the pumping volume 107 to a compressed or reduced state without the cooperation of the first plunger biasing member 164*a*.

During administration, the upstream portion 106 of the tubing 102 is blocked, pinched, or otherwise occluded by the upstream valve 120 to prevent or restrict inadvertent fluid flow into the pumping volume 107 and to prevent or restrict backflow of fluid into the medical container from the pumping volume 107.

During the compression of the pumping volume 107, medical fluid is forced from the pumping volume 107 to a downstream location through the downstream portion 108 of the tubing 102.

Figure 8A:
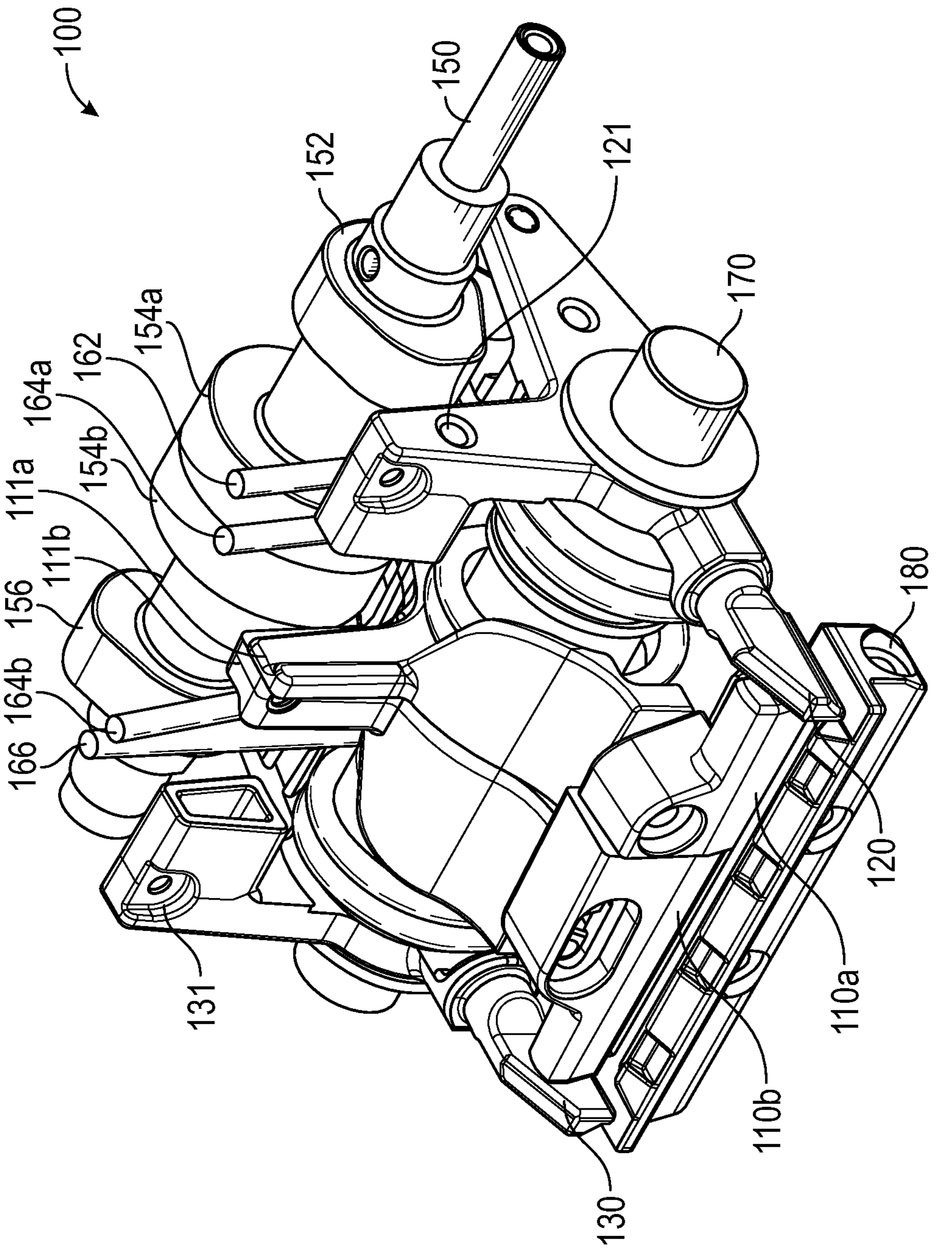
FIG. 8A is a simplified perspective view of a peristaltic pump, in accordance with various aspects of the present disclosure.
Figure 8B:
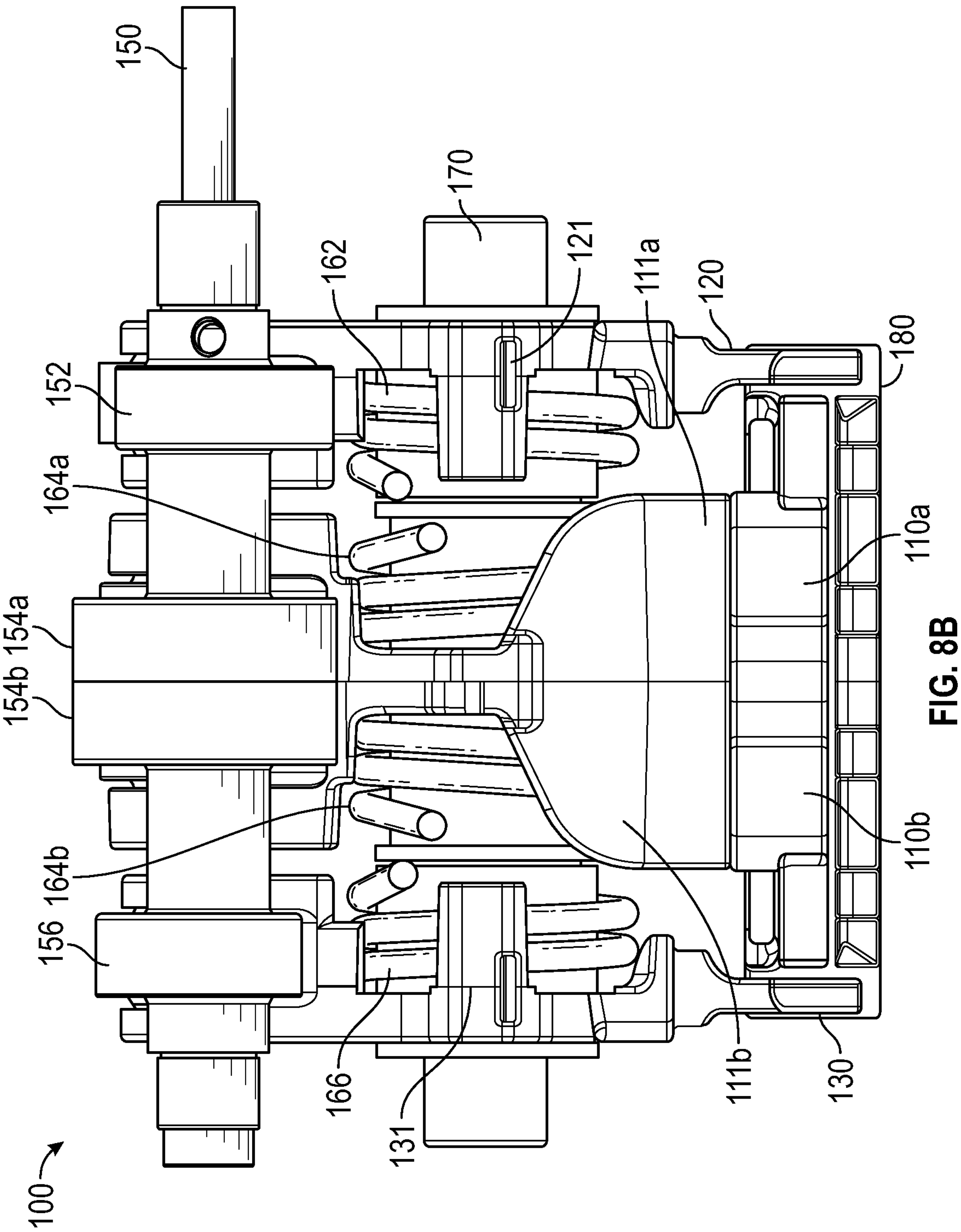
FIG. 8B is a top view of the peristaltic pump of FIG. 8A.
Figure 8C:
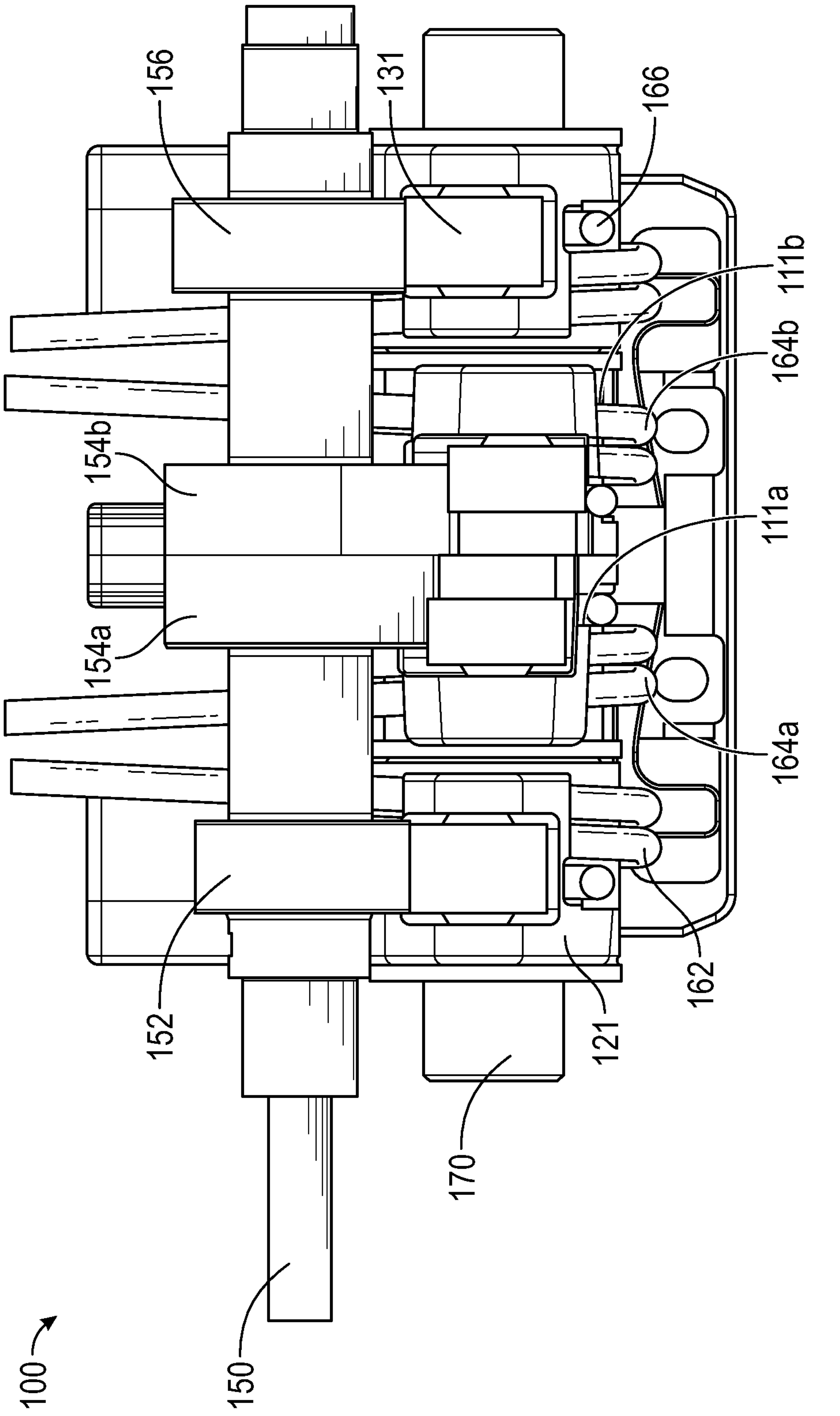
FIG. 8C is a back view of the peristaltic pump of FIG. 8A.

FIG. 8A is a simplified perspective view of a peristaltic pump 100, in accordance with various aspects of the present disclosure. FIG. 8B is a top view of the peristaltic pump 100 of FIG. 8A. FIG. 8C is a back view of the peristaltic pump 100 of FIG. 8A. With reference to FIGS. 8A-8C, the peristaltic pump 100 can independently control the operation of a first plunger 110*a* and a second plunger 110*b* to facilitate measurement of the volume within the tubing and to control the contact area and force applied to the tubing. Advantageously, the configuration of the peristaltic pump 100 can permit volume measurements without exerting excess force during a measurement phase.

In the depicted example, the peristaltic pump 100 includes a first plunger 110*a*, a second plunger 110*b*, an upstream occluder or valve 120, and a downstream occluder or valve 130, each configured to contact and manipulate the tubing to deliver fluid from a fluid source to the patient. In some embodiments, the first plunger 110*a*, the second plunger 110*b*, the upstream valve 120, and the downstream valve 130 can move in coordinated, sequential steps to pump fluid through the tubing.

In some embodiments, the first plunger 110*a* can be configured to contact the tubing to measure the volume within the pumping volume. The second plunger 110*b* can be configured to contact the tubing to administer fluid during a delivery phase of operation. As illustrated, the first plunger 110*a* and the second plunger 110*b* can have different geometries to vary the contact area in contact with the tubing during operation. As illustrated, the first plunger 110*a* can have a smaller contact area with the tubing compared to the second plunger 110*b*. In some embodiments, the first plunger 110*a* and the second plunger 110*b* can have similar or same sized contact areas. Further, as described herein, the first plunger 110*a* and the second plunger 110*b* can apply different or varying forces to the tubing.

As described herein, the first plunger 110*a*, the second plunger 110*b*, the upstream valve 120, and/or the downstream valve 130 can be moved by one or more actuators.

Figure 9:
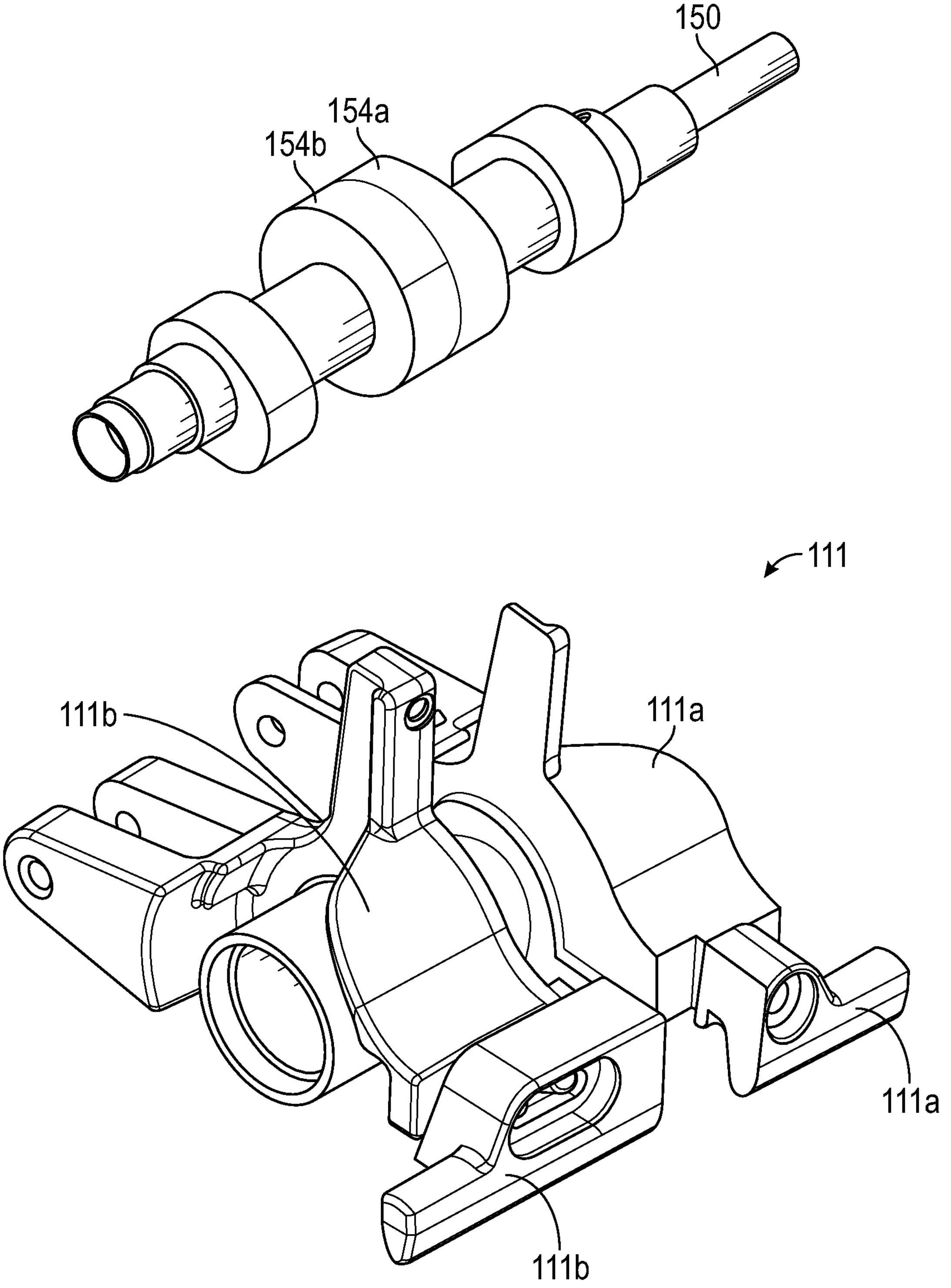
FIG. 9 is an exploded view of components of the peristaltic pump of FIG. 8A.

FIG. 9 is an exploded view of components of the peristaltic pump 100 of FIG. 8A.

As previously described, the peristaltic pump 100 can include a camshaft 150 to actuate the plunger 110, the upstream valve 120, and/or the downstream valve 130. In the depicted example, the camshaft 150 includes one or more cam lobes, such as a first plunger cam lobe 154*a*, a second plunger cam lobe 154*b*, an upstream valve cam lobe 152, and/or a downstream valve cam lobe 156.

In the depicted example, the peristaltic pump 100 includes a split rocker arrangement with a first plunger valve rocker 111*a* directly coupled to the first plunger 110*a* and a second plunger valve rocker 111*b* directly coupled to the second plunger 110*b*. In the depicted example, the first plunger valve rocker 111*a* is aligned, positioned, or otherwise configured to be actuated by the first plunger cam lobe 154*a*. During operation, a portion of the first plunger valve rocker 111*a* can engage or slide along the cam profile of the first plunger cam lobe 154*a* to translate the geometry of the cam profile into movement of the first plunger valve rocker 111*a* and the first plunger 110*a*. As can be appreciated, the first plunger valve rocker 111*a* and therefore the first plunger 110*a* may be independently moved or actuated separate from the actuation of the second plunger valve rocker 111*b* and the second plunger 110*b* during certain portions of operation (e.g., a measurement phase).

In the depicted example, a first plunger biasing member 164*a* can act upon the first plunger valve rocker 111*a* to urge the first plunger 110*a* toward the tubing and/or the backer 180. As can be appreciated, actuation of the first plunger valve rocker 111*a* by the rotation of the first plunger cam lobe 154*a* can overcome the biasing force to lift or otherwise actuate the first plunger 110*a* independent of the second plunger valve rocker 111*b* and the second plunger 110*b*. Therefore, the force applied to the first plunger 110*a* can vary in response to the actuation of the first plunger valve rocker 111*a* by the rotation of the first plunger cam lobe 154*a*.

During operation, the arrangement of the first plunger valve rocker 111*a*, the first plunger cam lobe 154*a*, and the first plunger biasing member 164*a* can allow the first plunger 110*a* to contact the tubing during a measurement phase with a reduced contact area and without administering the fluid within the pumping volume or damaging the tubing.

In the depicted example, the second plunger valve rocker 111*b* is aligned, positioned, or otherwise configured to be actuated by the second plunger cam lobe 154*b*. During operation, a portion of the second plunger valve rocker 111*b* can engage or slide along the cam profile of the second plunger cam lobe 154*b* to translate the geometry of the cam profile into movement of the second plunger valve rocker 111*b* and the second plunger 110*b*. As can be appreciated, the second plunger valve rocker 111*b* and therefore the second plunger 110*b* may be independently moved or actuated separate from the actuation of the first plunger valve rocker 111*a* and the first plunger 110*a* during certain portions of operation (e.g., a delivery phase). In some embodiments, during certain movements (e.g., during a delivery phase of operation) the second plunger valve rocker 111*b* can move in tandem with the first plunger valve rocker 111*a* to move both the first plunger 110*a* and the second plunger 110*b*.

In the depicted example, a second plunger biasing member 164*b* can act upon the second plunger valve rocker 111*b* to urge the second plunger 110*b* toward the tubing and/or the backer 180. As can be appreciated, actuation of the second plunger valve rocker 111*b* by the rotation of the second plunger cam lobe 154*b* can overcome the biasing force to lift or otherwise actuate the second plunger 110*b* independent of the first plunger valve rocker 111*a* and the first plunger 110*a*. Therefore, the force applied to the second plunger 110*b* can vary in response to the actuation of the second plunger valve rocker 111*b* by the rotation of the second plunger cam lobe 154*b*.

During operation, the arrangement of the second plunger valve rocker 111*b* and the second plunger biasing member 164*b* relative to the first plunger valve rocker 111*a* and the first plunger biasing member 164*a* allows the peristaltic pump 100 to apply additional force to the tubing via the first plunger 110*a* and the second plunger 110*b* during certain portions of operation (e.g., the delivery phase) while allowing the a reduced force via the first plunger 110*a* during other portions of operation (e.g., the measurement phase). In some embodiments, the force applied by the second plunger biasing member 164*b* to the second plunger 110*b* is higher than the biasing force applied by the first plunger biasing member 164*a* to the first plunger 110*a*. Optionally, the force applied by the second plunger biasing member 164*b* to the second plunger 110*b* is sufficient to allow fluid delivery. In some embodiments, the first plunger biasing member 164*a* and the second plunger biasing member 164*b* cooperatively provide sufficient force via the first plunger 110*a* and the second plunger 110*b* to allow for fluid delivery.

Further, the arrangement or phasing of the first plunger cam lobe 154*a* and the second plunger cam lobe 154*b* about the camshaft 150 can be modified to provide a desired sequence of actuation or movement of the first plunger 110*a* and the second plunger 110*b* as the camshaft 150 is rotated. For example, the cam lobes can each have a cam profile and/or a relative arrangement that includes a measurement phase that applies the first plunger 110*a* to the tubing with a reduced spring force and a delivery phase that applies the second plunger 110*b* with additional force.

Figures 10A, 10B, 10C, 10D:
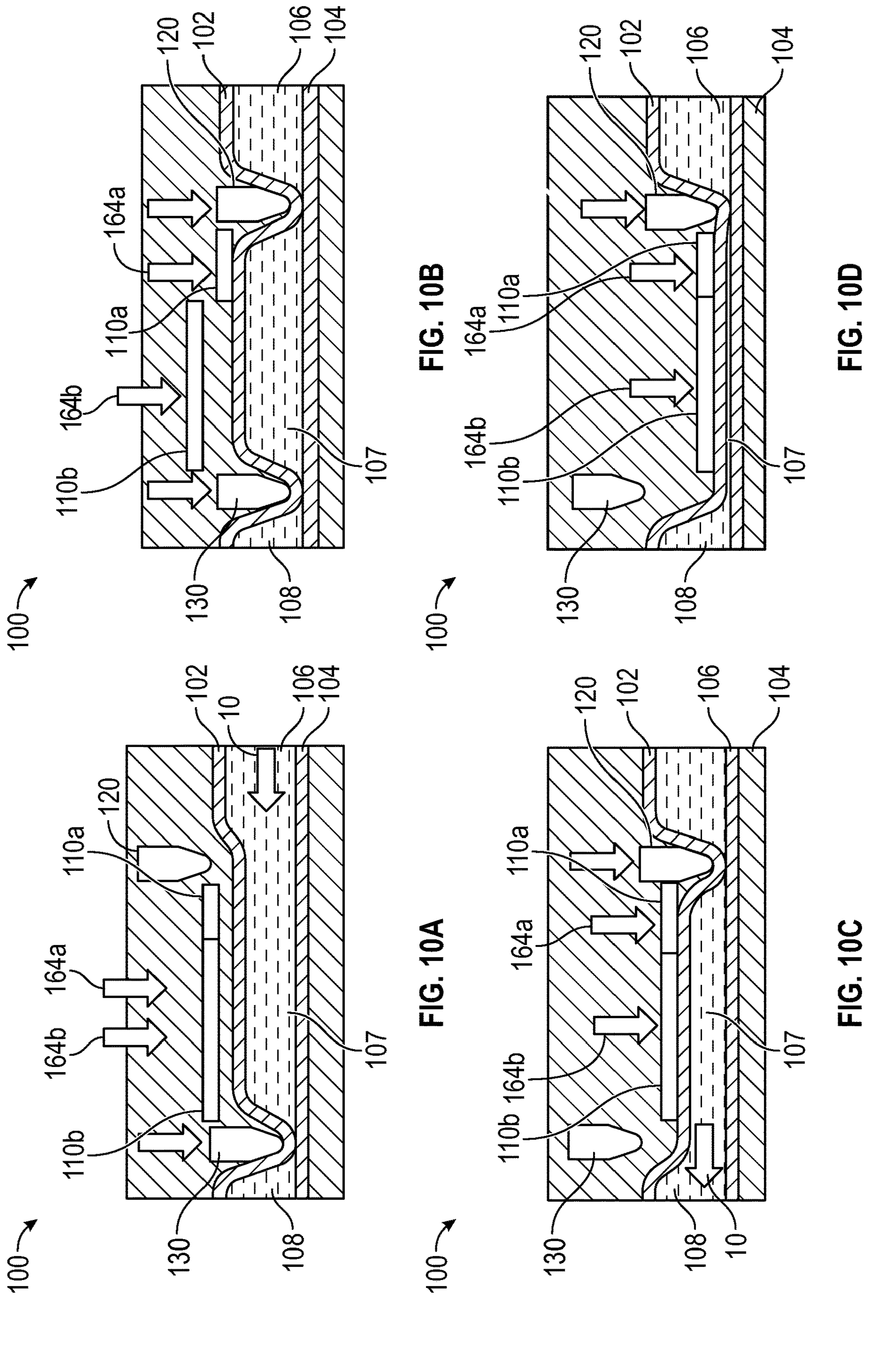
FIG. 10A is an illustration of the peristaltic pump of FIG. 8A in a filling phase, in accordance with various aspects of the present disclosure.
FIG. 10B is an illustration of the peristaltic pump of FIG. 8A in an initial position, in accordance with various aspects of the present disclosure.
FIG. 10C is an illustration of the peristaltic pump of FIG. 8A in a delivery phase, in accordance with various aspects of the present disclosure.
FIG. 10D is an illustration of the peristaltic pump of FIG. 8A in a delivered position, in accordance with various aspects of the present disclosure.

FIG. 10A is an illustration of the peristaltic pump 100 of FIG. 8A in a filling phase, in accordance with various aspects of the present disclosure. During operation, the tubing 102 draws in medical fluid 10 during the filling phase. As illustrated, the first plunger 110*a* and the second plunger 110*b* are withdrawn or retracted from a compressed portion of the tubing 102, allowing the tubing walls 104 to resiliently expand the pumping volume 107 to an original or expanded state.

In the depicted example, the expansion of the pumping volume 107 draws in fluid into the pumping volume 107. As illustrated, during the expansion of the pumping volume 107, the downstream portion 108 of the tubing 102 is blocked, pinched, or otherwise occluded by the downstream valve 130 to prevent or restrict backflow or contamination of fluid into the pumping volume 107.

During the expansion of the pumping volume 107, medical fluid 10 is drawn into pumping volume 107 from the upstream portion 106 of the tubing 102. As illustrated, during the expansion of the pumping volume 107, the upstream portion 106 of the tubing 102 is unobstructed by the upstream valve 120, permitting medical fluid 10 into the pumping volume 107. During operation, the upstream valve 120 is withdrawn or retracted from a compressed portion of the tubing 102, allowing the tubing walls 104 to resiliently expand the upstream portion 106 to an original or expanded state.

In the depicted example, the expansion of the upstream portion 106 permits the flow of medical fluid 10 into the pumping volume 107. Advantageously, and as described herein, the arrangement of the first plunger cam lobe 154*a* and the second plunger cam lobe 154*b* can prevent the first plunger biasing member 164*a* and the second plunger biasing member from applying force to the first plunger 110*a*, the second plunger 110*b*, and/or the tubing 102 during the filling phase.

FIG. 10B is an illustration of the peristaltic pump 100 of FIG. 8A in a measurement position, in accordance with various aspects of the present disclosure. After filling, the volume of medical fluid within the pumping volume 107 can be measured. As illustrated, the first plunger 110*a* is used to measure the height of the pumping volume 107 and/or the tubing 102 to determine the volume of medical fluid within the pumping volume 107.

During the measurement phase, the downstream portion 108 of the tubing 102 remains blocked, pinched, or otherwise occluded by the downstream valve 130 to prevent or restrict backflow or contamination of fluid into the pumping volume 107. Further, the upstream portion 106 of the tubing 102 is blocked, pinched, or otherwise occluded by the upstream valve 120 to prevent or restrict inadvertent fluid flow into the pumping volume 107 and to prevent or restrict backflow of fluid into the medical container from the pumping volume 107.

Further, during measurement, the first plunger biasing member 164*a* applies a force to the first plunger 110*a* to allow the first plunger 110*a* to contact the tubing 102 to determine the height of the tubing 102 and/or the pumping volume 107. In the depicted example, the force applied by the first plunger biasing member 164*a* via the first plunger 110*a* can be sufficient to maintain contact with the tubing 102 without creating excess pressure within the pumping volume.

FIG. 10C is an illustration of the peristaltic pump 100 of FIG. 8A in a delivery phase, in accordance with various aspects of the present disclosure. FIG. 10D is an illustration of the peristaltic pump 100 of FIG. 8A in a delivered position, in accordance with various aspects of the present disclosure. With reference to FIGS. 10C and 10D, the peristaltic pump 100 delivers medical fluid through a downstream portion 108 to a downstream location, such as a patient. As illustrated, the first plunger 110*a* and the second plunger 110*b* are actuated, moved downward, or otherwise engaged to compress the tubing walls 104 of the tubing 102 to compress the pumping volume 107 to a compressed or reduced state.

During operation, the compression of the pumping volume 107 expels or otherwise administers fluid from the pumping volume 107 to a downstream location. The rate of administration of the medical fluid can be controlled by the force and velocity of the first plunger 110*a* and the second plunger 110*b*.

As described herein, the first plunger biasing member 164*a* and the second plunger biasing member 164*b* cooperatively force the first plunger 110*a* and the second plunger 110*b*, respectively, to compress the pumping volume 107 to a compressed or reduced state. In some embodiments, the second plunger biasing member 164*b* can force the second plunger 110*b* to compress the pumping volume 107 to a compressed or reduced state without the cooperation of the first plunger biasing member 164*a* or the first plunger 110*a*.

During administration, the upstream portion 106 of the tubing 102 is blocked, pinched, or otherwise occluded by the upstream valve 120 to prevent or restrict inadvertent fluid flow into the pumping volume 107 and to prevent or restrict backflow of fluid into the medical container from the pumping volume 107.

During the compression of the pumping volume 107, medical fluid is forced from the pumping volume 107 to a downstream location through the downstream portion 108 of the tubing 102.

Figure 11A:
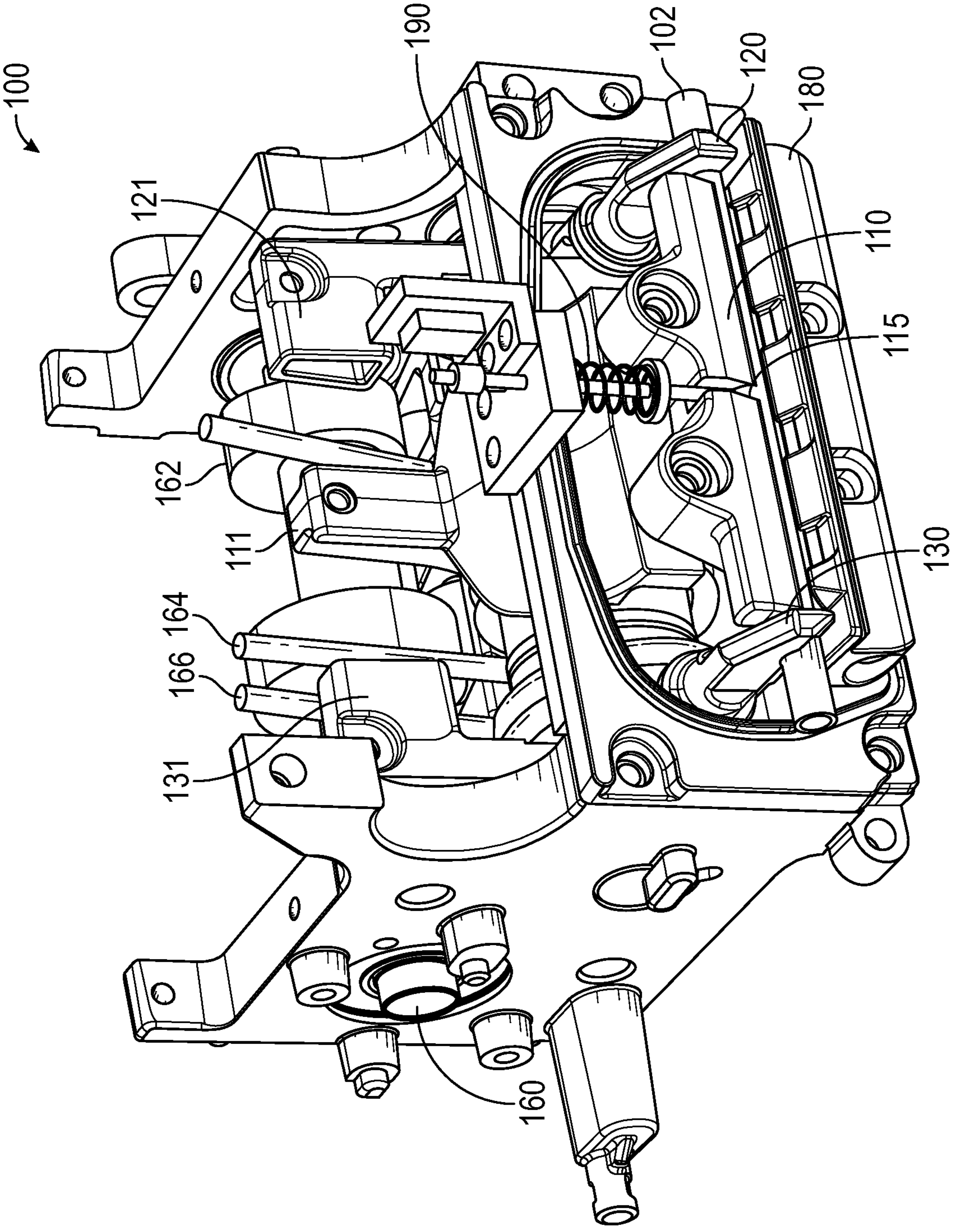
FIG. 11A is a perspective view of a peristaltic pump, in accordance with various aspects of the present disclosure.
Figure 11B:
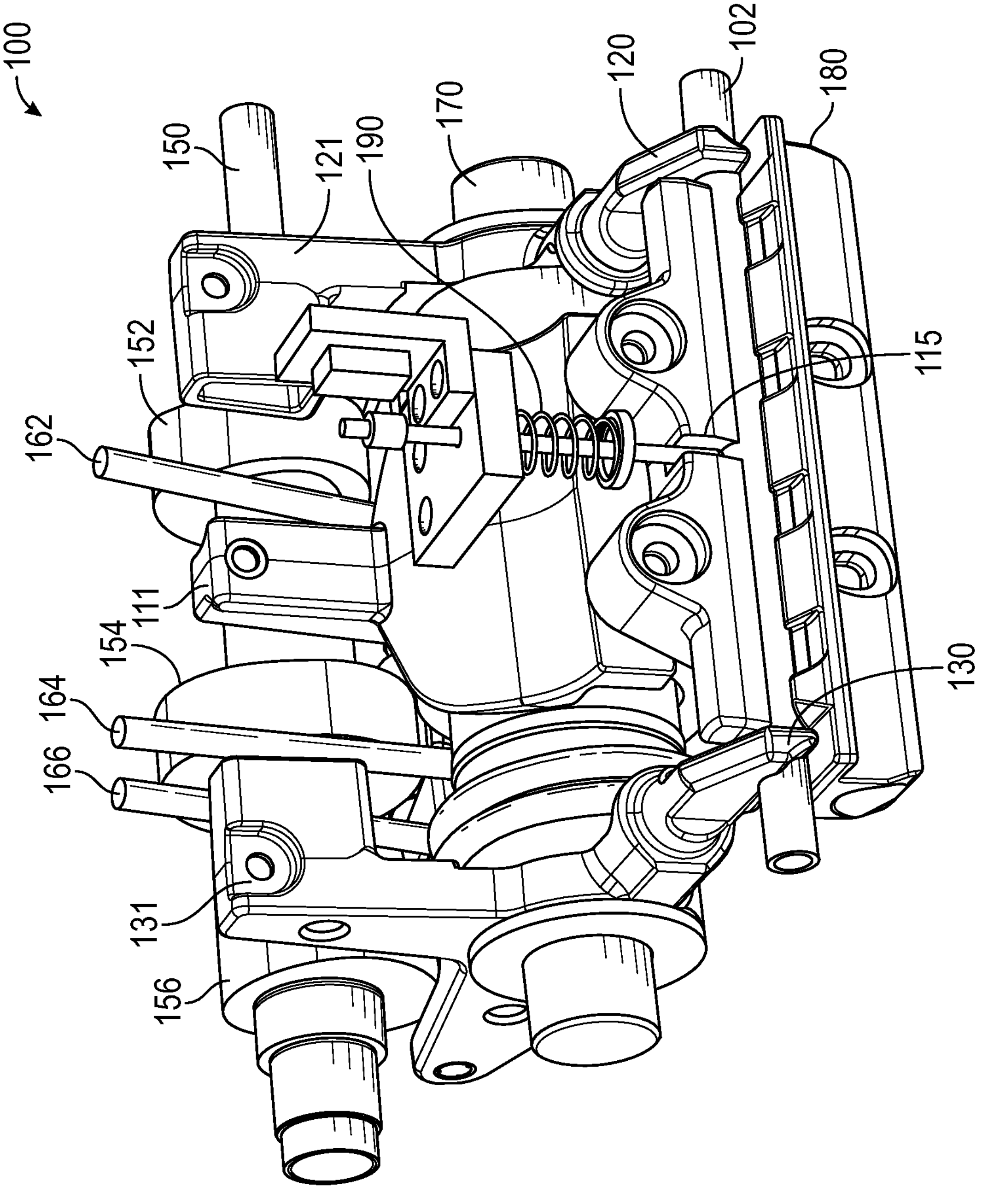
FIG. 11B is a simplified view of the peristaltic pump of FIG. 11A.

FIG. 11A is a perspective view of a peristaltic pump 100, in accordance with various aspects of the present disclosure. FIG. 11B is a simplified view of the peristaltic pump 100 of FIG. 11A. In the depicted example, the peristaltic pump 100 includes a feeler pin 190 to measure the volume of the fluid being delivered to the patient. In the depicted example, the peristaltic pump 100 includes a plunger 110, an upstream occluder or valve 120, and a downstream occluder or valve 130, each configured to contact and manipulate the tubing to deliver fluid from a fluid source to the patient. Advantageously, the configuration of the peristaltic pump 100 can permit volume measurements without a dedicated measurement phase.

In the depicted example, the peristaltic pump 100 can include a camshaft 150 to actuate the plunger 110, the upstream valve 120, and/or the downstream valve 130. In the depicted example, the camshaft 150 includes one or more cam lobes, such as a plunger cam lobe 154, an upstream valve cam lobe 152, and/or a downstream valve cam lobe 156.

As described herein, the geometry of the respective cam lobes can be shaped or modified to allow for a desired actuation or movement of the plunger 110, the upstream valve 120, and/or the downstream valve 130. In some embodiments, the cam lobes of the camshaft 150 actuate one or more rockers to control the plunger 110, the upstream valve 120, and/or the downstream valve 130.

In the depicted example, biasing members, such as springs can urge the plunger 110, the upstream valve 120, and/or the downstream valve 130 toward the tubing and/or the backer 180.

Further, the arrangement or phasing of the cam lobes about the camshaft 150 can be modified to provide a desired sequence of actuation or movement of the plunger 110, the upstream valve 120, and/or the downstream valve 130 as the camshaft 150 is rotated. For example, the plunger cam lobe 154, the upstream valve cam lobe 152, and/or the downstream valve cam lobe 156 can each have a cam profile and/or a relative arrangement that eliminates or otherwise does not include a dedicated measurement phase where the plunger 110 is actuated against a pumping volume of the tubing closed by the upstream valve 120 and the downstream valve 130.

In the depicted example, the peristaltic pump 100 includes a single rocker arrangement with a plunger valve rocker 111 directly coupled to the plunger 110. In the depicted example, the plunger valve rocker 111 is aligned, positioned, or otherwise configured to be actuated by the plunger cam lobe 154. During operation, a portion of the plunger valve rocker 111 can engage or slide along the cam profile of the plunger cam lobe 154 to translate the geometry of the cam profile into movement of the plunger valve rocker 111 and the plunger 110. In the depicted example, a plunger biasing member 164 can act upon the plunger valve rocker 111 to urge the plunger 110 toward the tubing and/or the backer 180. As can be appreciated, actuation of the plunger valve rocker 111 by the rotation of the plunger cam lobe 154 can overcome the biasing force to lift or otherwise actuate the plunger 110. Therefore, the force applied to the plunger 110 can vary in response to the actuation of the plunger valve rocker 111 by the rotation of the plunger cam lobe 154.

In some embodiments, an upstream valve rocker 121 is coupled to the upstream valve 120 and can move the upstream valve 120 in response to actuation from the upstream valve cam lobe 152. As illustrated, an upstream valve biasing member 162 can act upon the upstream valve rocker 121 to urge the upstream valve 120 toward the tubing and/or the backer 180.

Similarly, a downstream valve rocker 131 is coupled to the downstream valve 130 and can move the downstream valve 130 in response to actuation from the downstream valve cam lobe 156. Similarly, a downstream valve biasing member 166 can act upon the downstream valve rocker 131 to urge the downstream valve 130 toward the tubing and/or the backer 180.

Figure 12:
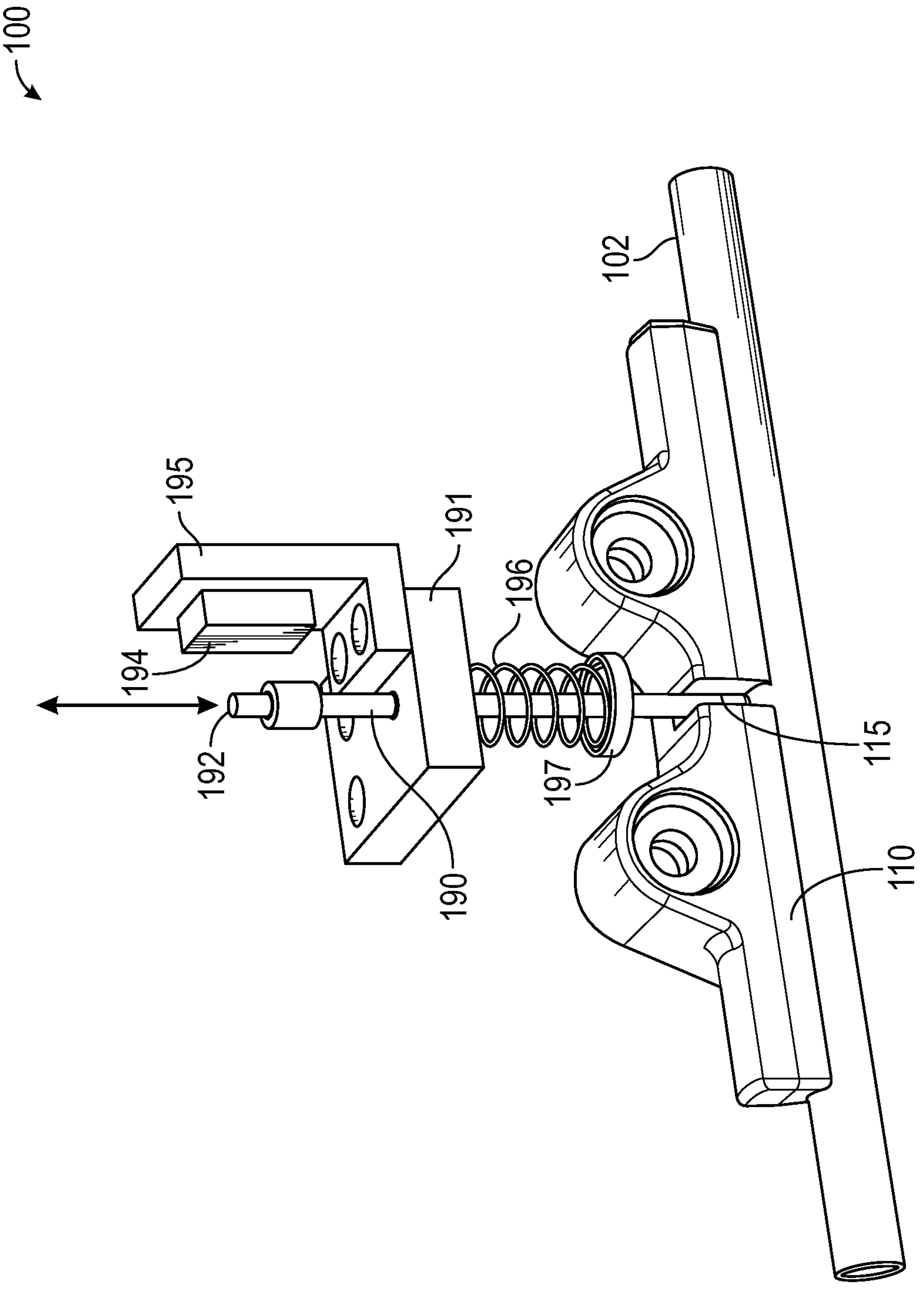
FIG. 12 is a perspective view of the feeler pin of the peristaltic pump of FIG. 11A.

FIG. 12 is a perspective view of the feeler pin 190 of the peristaltic pump 100 of FIG. 11A. With reference to FIGS. 11A, 11B, and 12, the feeler pin 190 can determine the volume of fluid administered by the peristaltic pump 100. During operation, the feeler pin 190 can be used to determine the height of the pumping volume within the tubing 102, which can be used to determine the volume of the fluid administered by the peristaltic pump 100.

In the depicted example, the feeler pin 190 can extend through the plunger 110 to contact the tubing 102 disposed between the plunger 110 and the backer 180. As illustrated, the feeler pin 190 can extend through a slot 115 formed through the plunger 110. In some embodiments, the feeler pin 190 has a rounded tip to contact the tubing 102.

During operation, the feeler pin 190 can move with the tubing 102 as the height of the pumping volume changes. In some embodiments, the feeler pin 190 can include a biasing member 196 configured to urge the feeler pin 190 toward the tubing 102, allowing the feeler pin 190 to maintain contact with the tubing during operation. As can be appreciated, the biasing force of the biasing member 196 can be sufficient to maintain contact with the tubing 102 without exerting excess force on the tubing. Optionally, the biasing member 196 can exert the biasing force against the feeler pin 190 via a feeler plate 197. An opposite end of the biasing member 196 can engage against a feeler pin bracket 191.

In some embodiments, the feeler pin 190 is coupled to the peristaltic pump 100 via the feeler pin bracket 191. The feeler pin bracket 191 can include a passage to support the feeler pin 190 during operation. Optionally, the feeler pin bracket 191 can constrain the movement of the feeler pin 190 in a single measurement direction. For example, the feeler pin bracket 191 can constrain the movement of the feeler pin 190 in an axis perpendicular to the longitudinal axis of the tubing 102.

In the depicted example, the peristaltic pump 100 can measure the position or height of the feeler pin 190 to determine the height of the pumping volume in the tubing 102. As illustrated, the peristaltic pump 100 can include a position transducer 194 to detect the position of the feeler pin 190. The feeler pin 190 can include a trigger portion 192 that provide a signal or identifiable portion of the position transducer 194. Optionally, the trigger portion 192 can be magnetic and provide a signal to the position transducer 194. The position transducer 194 can be mounted parallel to the direction of travel of the feeler pin 190 via a mounting bracket 195. The height or position of the feeler pin 190 can be utilized to determine the volume of the pumping volume within the tubing 102.

Figure 13A:
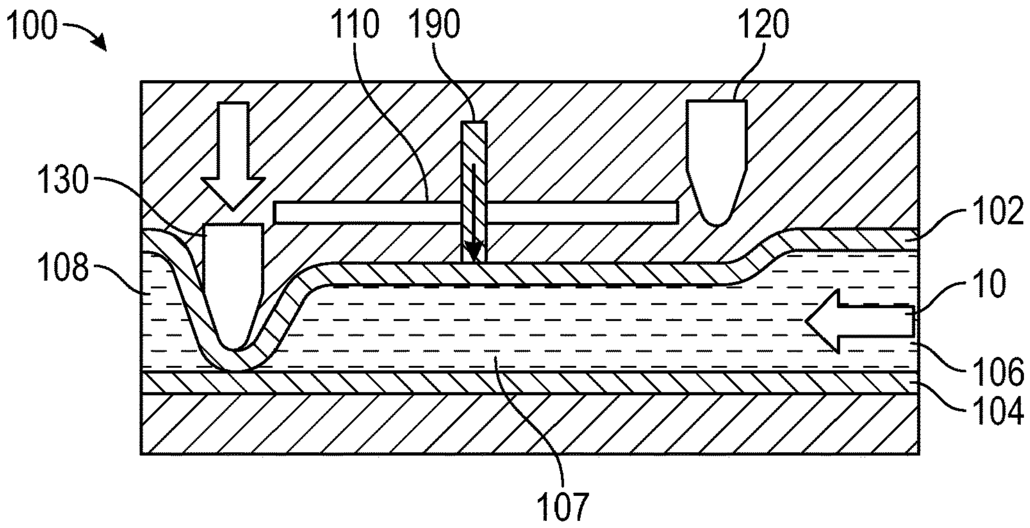
FIG. 13A is an illustration of the peristaltic pump of FIG. 11A in a filling phase, in accordance with various aspects of the present disclosure.

FIG. 13A is an illustration of the peristaltic pump 100 of FIG. 11A in a filling phase, in accordance with various aspects of the present disclosure. During operation, the tubing 102 draws in medical fluid 10 during the filling phase. In the depicted example, the expansion of the pumping volume 107 draws in fluid into the pumping volume 107.

As illustrated, during the expansion of the pumping volume 107, the downstream portion 108 of the tubing 102 is blocked, pinched, or otherwise occluded by the downstream valve 130 to prevent or restrict backflow or contamination of fluid into the pumping volume 107.

In the depicted example, the downstream valve 130 is actuated, moved downward, or otherwise engaged to compress the tubing walls 104 of the tubing 102 at the downstream portion 108 to occlude flow through the downstream portion 108 of the tubing 102. During the expansion of the pumping volume 107, medical fluid 10 is drawn into pumping volume 107 from the upstream portion 106 of the tubing 102.

In the depicted example, the expansion of the upstream portion 106 permits the flow of medical fluid 10 into the pumping volume 107. Advantageously, and as described herein, the feeler pin 190 can extend through the plunger 110 to maintain contact with the tubing 102 during the filling phase to permit measurement of the pumping volume. In the depicted example, the force applied by the biasing member 196 can be sufficient to maintain contact with the tubing 102 while allowing for the pumping volume 107 to be filled.

Figure 13B:
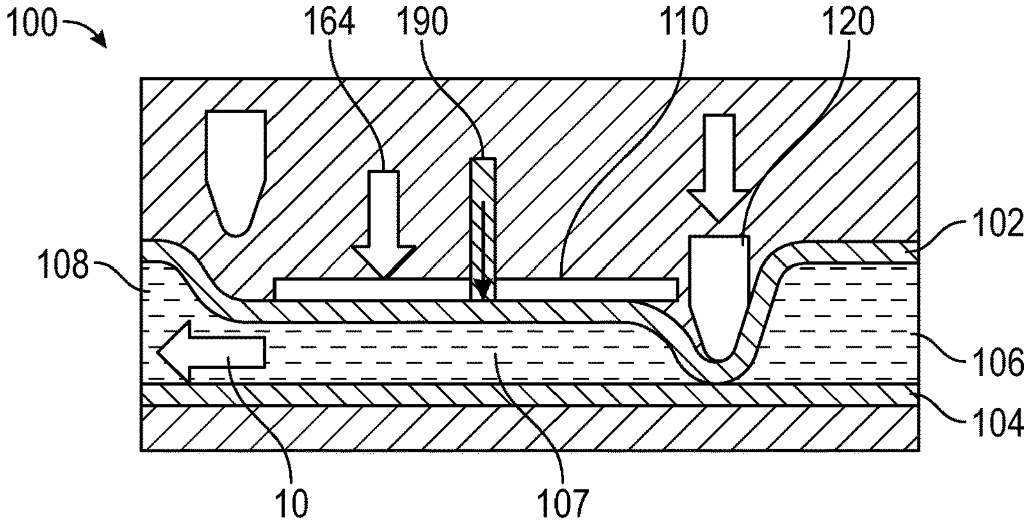
FIG. 13B is an illustration of the peristaltic pump of FIG. 11A in a delivery phase, in accordance with various aspects of the present disclosure.
Figure 13C:
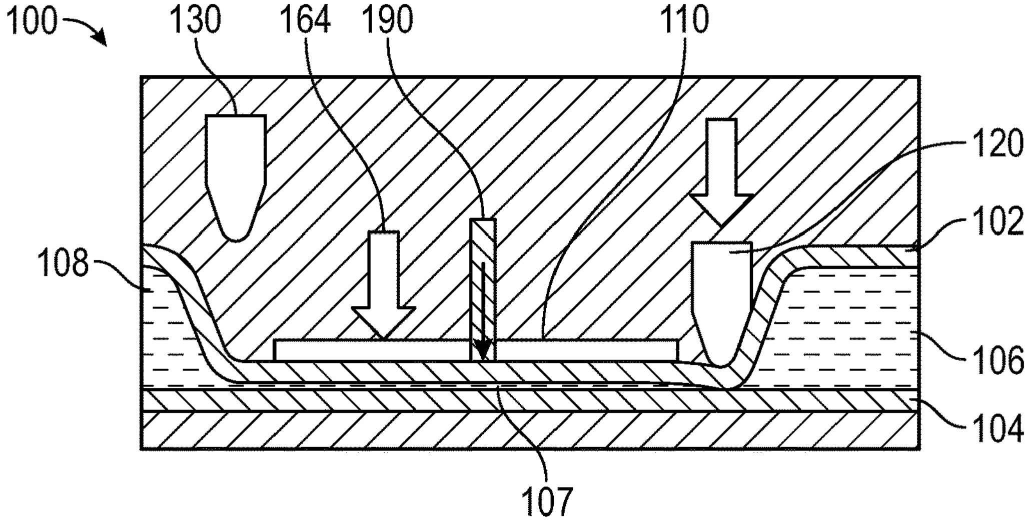
FIG. 13C is an illustration of the peristaltic pump of FIG. 11A in a delivered position, in accordance with various aspects of the present disclosure.

FIG. 13B is an illustration of the peristaltic pump 100 of FIG. 11A in a delivery phase, in accordance with various aspects of the present disclosure. FIG. 13C is an illustration of the peristaltic pump 100 of FIG. 11A in a delivered position, in accordance with various aspects of the present disclosure. With reference to FIGS. 13B and 13C, the peristaltic pump 100 delivers medical fluid through a downstream portion 108 to a downstream location, such as a patient. As illustrated, the plunger 110 is actuated, moved downward, or otherwise engaged to compress the tubing walls 104 of the tubing 102 to compress the pumping volume 107 to a compressed or reduced state.

During operation, the compression of the pumping volume 107 expels or otherwise administers fluid from the pumping volume 107 to a downstream location. As described herein, the plunger biasing member 164 force the plunger 110 to compress the pumping volume 107 to a compressed or reduced state.

During administration, the upstream portion 106 of the tubing 102 is blocked, pinched, or otherwise occluded by the upstream valve 120 to prevent or restrict inadvertent fluid flow into the pumping volume 107 and to prevent or restrict backflow of fluid into the medical container from the pumping volume 107.

In the depicted example, the upstream valve 120 is actuated, moved downward, or otherwise engaged to compress the tubing walls 104 of the tubing 102 at the upstream portion 106 to occlude flow through the upstream portion 106 of the tubing 102. During the compression of the pumping volume 107, medical fluid is forced from the pumping volume 107 to a downstream location through the downstream portion 108 of the tubing 102.

In the depicted example, the expansion of the downstream portion 108 permits the flow of medical fluid 10 out of the pumping volume 107. The amount of medical fluid 10 administered from the pumping volume 107 during the delivery phase can be determined by the timing and sequence of the plunger 110, the downstream valve 130 and the mechanical properties of the tubing 102.

Advantageously, and as described herein, the feeler pin 190 can maintain contact with the tubing 102 during the delivery phase to permit measurement of the pumping volume during the entire cycle, providing more information to a clinician without interrupting fluid delivery.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A peristaltic pump comprising:

a plunger movable to selectively engage a pumping volume of a tubing segment to expand the pumping volume to draw fluid flow into the pumping volume and to contract the pumping volume to conduct fluid flow from the pumping volume;

a first biasing member configured to urge the plunger toward the tubing segment to maintain contact with the tubing segment during the expansion of the pumping volume;

a second biasing member configured to urge the plunger toward the tubing segment to contract the pumping volume; and a first rocker coupled to the first biasing member and a separate second rocker coupled to the second biasing member, the first rocker and the second rocker being moveable independently of each other, wherein the first biasing member and the second biasing member are configured to cooperatively urge the plunger toward the tubing segment to contract the pumping volume, and the first biasing member has a first biasing force and the second biasing member has a second biasing force, wherein the first biasing force is less than the second biasing force.

2. The peristaltic pump of claim 1, wherein the second rocker is coupled to the plunger.

3. The peristaltic pump of claim 2, wherein the first rocker is configured to contact the second rocker to urge the plunger toward the tubing segment.

4. A peristaltic pump comprising:

a plunger movable to selectively engage a pumping volume of a tubing segment;

a camshaft comprising a plunger cam lobe, wherein the plunger cam lobe is configured to move the plunger between an expansion position to draw fluid flow into the pumping volume and a contraction position to conduct fluid flow from the pumping volume;

a split rocker comprising a first rocker and a second rocker each coupled to and independently rotatable about a pivot shaft; and a first biasing member configured to urge the plunger toward the tubing segment independent of rotation of the camshaft to maintain contact with the tubing segment during the expansion of the pumping volume.

5. The peristaltic pump of claim 4, further comprising a second biasing member configured to urge the plunger toward the tubing segment to contract the pumping volume.

6. The peristaltic pump of claim 5, further comprising the first rocker coupled to the first biasing member and the second rocker coupled to the second biasing member, wherein the second rocker is actuated by the plunger cam lobe.

7. The peristaltic pump of claim 6, wherein the second rocker is coupled to the plunger.

8. The peristaltic pump of claim 7, wherein the first rocker is configured to contact the second rocker to urge the plunger toward the tubing segment.

9. The peristaltic pump of claim 5, wherein the first biasing member and the second biasing member are configured to cooperatively urge the plunger toward the tubing segment to contract the pumping volume.

10. The peristaltic pump of claim 4, further comprising:

an upper valve movable to selectively engage an upstream portion of the tubing segment; and a lower valve movable to selectively engage a downstream portion of the tubing segment, wherein the upper valve is configured to engage the upstream portion of the tubing segment when the plunger is in the contraction position, and the lower valve is configured to be spaced apart from the downstream portion of the tubing segment when the plunger is in the contraction position.

11. The peristaltic pump of claim 10, wherein the lower valve is configured to engage the downstream portion of the tubing segment when the plunger is in the expansion position and the upper valve is configured to be spaced apart from the upstream portion of the tubing segment when the plunger is in the expansion position.

* * * * *